United States Patent [19]

Grace

[11] Patent Number: 5,400,428
[45] Date of Patent: Mar. 21, 1995

[54] METHOD AND APPARATUS FOR LINEARLY SCANNING ENERGY OVER AN OPTICAL FIBER ARRAY AND COUPLER FOR COUPLING ENERGY TO THE OPTICAL FIBER ARRAY

[75] Inventor: Kenneth P. Grace, Woodland Park, Colo.

[73] Assignee: Spectranetics Corporation, Colorado Springs, Colo.

[21] Appl. No.: 205,143

[22] Filed: Mar. 2, 1994

Related U.S. Application Data

[63] Continuation of Ser. No. 882,597, May 13, 1992, abandoned.

[51] Int. Cl.$^6$ .................. G02B 6/04; A61B 17/36
[52] U.S. Cl. .................. 385/115; 385/38; 385/116; 385/119; 385/147; 606/7; 606/11; 606/15; 606/16; 128/898
[58] Field of Search .................. 385/60, 66, 78, 80, 385/88, 89, 38, 139, 76, 115, 116, 117, 119, 118, 120, 147; 606/7, 11, 14, 15, 16; 372/57; 128/4, 6, 362, 395, 421

[56] References Cited

U.S. PATENT DOCUMENTS

| | | | |
|---|---|---|---|
| 3,262,359 | 7/1966 | Carpenter | 359/754 X |
| 3,799,657 | 3/1974 | Dager et al. | 219/121 L |
| 3,873,211 | 3/1975 | Watson | 356/156 |
| 3,984,171 | 10/1976 | Hotchkiss | 178/7.6 X |
| 4,007,377 | 2/1977 | Simon et al. | 250/566 |
| 4,024,545 | 5/1977 | Dowling et al. | 346/76 L |
| 4,099,829 | 7/1978 | Straayer | 350/6.1 |
| 4,189,752 | 2/1980 | Moe et al. | 358/298 |
| 4,195,269 | 3/1980 | Ettenberg et al. | 332/7.51 |
| 4,218,112 | 8/1980 | Ruker | 250/234 X |
| 4,272,151 | 6/1981 | Balasubramanian | 250/236 X |
| 4,312,590 | 1/1982 | Harbaugh | 355/51 |
| 4,323,307 | 4/1982 | Seeley | 355/51 |
| 4,350,867 | 9/1982 | Kinoshita et al. | 219/121 LC |
| 4,355,859 | 10/1982 | Herloski et al. | 356/153 X |
| 4,385,832 | 5/1983 | Doi et al. | 356/73.1 |
| 4,439,157 | 3/1984 | Breglia et al. | 434/44 |
| 4,482,902 | 11/1984 | Bailey et al. | 346/108 |
| 4,491,463 | 1/1985 | Weinstein et al. | 65/2 |
| 4,552,578 | 11/1985 | Anderson | 65/29 |
| 4,556,284 | 12/1985 | Albersdoerfer et al. | 385/115 X |
| 4,556,875 | 12/1985 | Ishiwatari | 128/303.1 X |
| 4,575,181 | 3/1986 | Ishikawa | 385/33 X |
| 4,588,887 | 5/1986 | Bailey et al. | 250/236 |
| 4,614,868 | 9/1986 | Alster | 250/227.11 X |
| 4,638,456 | 1/1987 | Elias et al. | 364/518 |
| 4,641,912 | 2/1987 | Goldenberg | 385/33 X |
| 4,655,590 | 4/1987 | Aagano et al. | 356/72 |
| 4,681,396 | 7/1987 | Jones | 372/6 X |
| 4,686,363 | 8/1987 | Schoon | 250/235 |
| 4,712,887 | 12/1987 | Baer | 369/44 X |
| 4,717,222 | 1/1988 | Iwasaki et al. | 355/66 X |
| 4,728,187 | 3/1988 | Dubroeucq et al. | 356/153 |
| 4,732,448 | 3/1988 | Goldenberg | 219/121 LX |
| 4,736,744 | 4/1988 | Koike et al. | 128/303.1 |
| 4,739,162 | 4/1988 | Ortiz, Jr. et al. | 250/227.11 X |
| 4,744,627 | 5/1988 | Chande et al. | 385/137 X |

(List continued on next page.)

FOREIGN PATENT DOCUMENTS

| | | | |
|---|---|---|---|
| 55-67721 | 5/1980 | Japan | 385/33 X |
| 2144873 | 3/1985 | United Kingdom | 385/33 X |

OTHER PUBLICATIONS

Technolas Laser Technik GmbH, "SELCA-The Smooth Revolution . . .", advertising literature received at Cardiology Convention some time before Apr. 27, 1992.

Primary Examiner—Brian Healy
Attorney, Agent, or Firm—Cushman, Darby & Cushman

[57] ABSTRACT

A method and apparatus for relatively moving energy across an array of optical fibers. The energy may be scanned across the fiber array. A dielectric mirror mounted on a galvanometer scanner is moved so as to cause successive pulses to irradiate different segments of the fiber optic array. As a result, each fiber receives radiation having sufficient fluence while reducing the energy per pulse (or the cw equivalent). Rather, than move the energy across the fiber array, the fiber array itself may be moved. One possible manner of movement is use of a piezo electric stack.

116 Claims, 13 Drawing Sheets

U.S. PATENT DOCUMENTS

| | | | |
|---|---|---|---|
| 4,751,525 | 6/1988 | Robinson | 346/108 |
| 4,762,994 | 8/1988 | Byerly et al. | 250/236 |
| 4,784,132 | 11/1988 | Fox et al. | 128/303.1 |
| 4,795,227 | 1/1989 | Chande | 385/33 X |
| 4,799,754 | 1/1989 | Goldenberg | 606/21 X |
| 4,806,728 | 2/1989 | Salzer et al. | 219/121.63 |
| 4,812,641 | 3/1989 | Ortiz, Jr. | 219/121.62 |
| 4,829,529 | 5/1989 | Kafka | 372/6 |
| 4,830,443 | 5/1989 | Hecker et al. | 350/3.71 |
| 4,838,631 | 6/1989 | Chande et al. | 219/121.77 X |
| 4,847,462 | 7/1989 | Soodak et al. | 219/121.63 |
| 4,896,944 | 1/1990 | Irwin et al. | 219/121.7 |
| 4,900,138 | 2/1990 | Atkinson, III et al. | 360/417 X |
| 4,913,142 | 4/1990 | Kittrell et al. | 606/7 |
| 4,917,084 | 4/1990 | Sinofsky | 606/7 |
| 4,919,508 | 4/1990 | Grace et al. | 128/303.1 X |
| 4,925,265 | 5/1990 | Rink et al. | 385/33 X |
| 4,950,266 | 9/1990 | Sinofsky | 606/2 |
| 4,967,745 | 11/1990 | Hayes et al. | 606/15 X |
| 4,994,059 | 2/1991 | Kosa et al. | 606/12 |
| 4,998,794 | 3/1991 | Holzman | 385/31 X |
| 5,007,691 | 4/1991 | Bobba et al. | 346/160 X |
| 5,012,087 | 4/1991 | Rockstroh et al. | 250/227.15 |
| 5,013,120 | 5/1991 | Gergely et al. | 356/318 |
| 5,016,964 | 5/1991 | Donnelly | 385/115 X |
| 5,032,123 | 7/1991 | Katz et al. | 606/15 |
| 5,034,010 | 7/1991 | Kittrell et al. | 606/15 |
| 5,044,717 | 9/1991 | Levatter | 385/33 |
| 5,054,877 | 10/1991 | Ortiz, Jr. et al. | 385/33 |
| 5,074,628 | 12/1991 | Khattak et al. | 359/205 X |
| 5,084,883 | 1/1992 | Khalid et al. | 372/24 |
| 5,086,474 | 1/1992 | Miyamoto | 359/648 X |
| 5,139,494 | 8/1992 | Freiberg | 606/3 |
| 5,159,402 | 10/1992 | Ortiz, Jr. | 356/237 |
| 5,159,483 | 10/1992 | Watanabe et al. | 359/210 |
| 5,159,656 | 10/1992 | Goldstein | 385/115 X |
| 5,173,583 | 12/1992 | de Contencin et al. | 219/121.74 |
| 5,178,617 | 1/1993 | Kuizenga et al. | 606/17 |
| 5,181,137 | 1/1993 | Koide | 359/217 |
| 5,188,632 | 2/1993 | Goldenberg | 606/7 |
| 5,196,004 | 3/1993 | Sinofsky | 606/3 |
| 5,196,005 | 3/1993 | Doiron et al. | 385/115 X |
| 5,206,869 | 4/1993 | Khalid et al. | 372/24 |
| 5,227,910 | 7/1993 | Khattak | 359/211 |
| 5,237,634 | 8/1993 | Follis | 385/31 |
| 5,242,438 | 9/1993 | Saadatmanesh et al. | 606/15 |
| 5,245,682 | 9/1993 | Ortiz, Jr. | 385/33 |
| 5,250,045 | 10/1993 | Bohley | 606/7 |
| 5,253,312 | 10/1993 | Payne et al. | 385/31 |

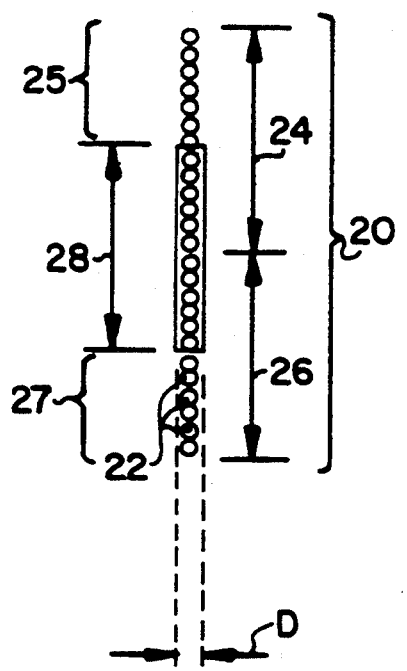
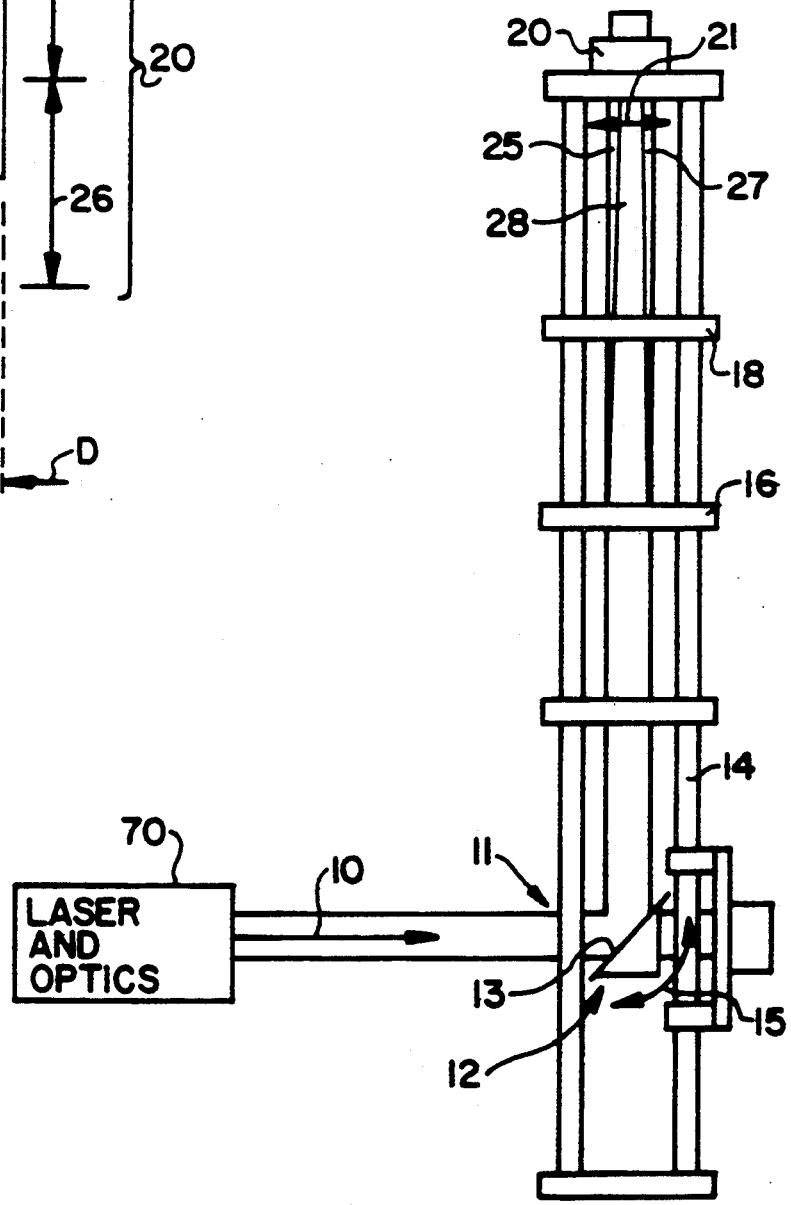

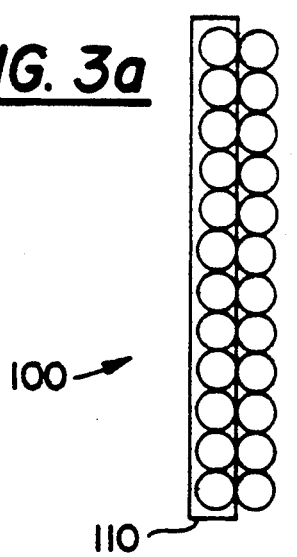
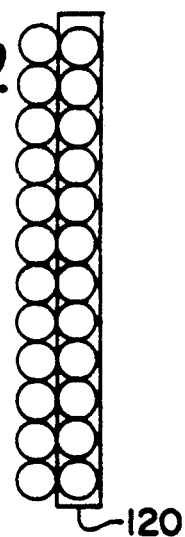
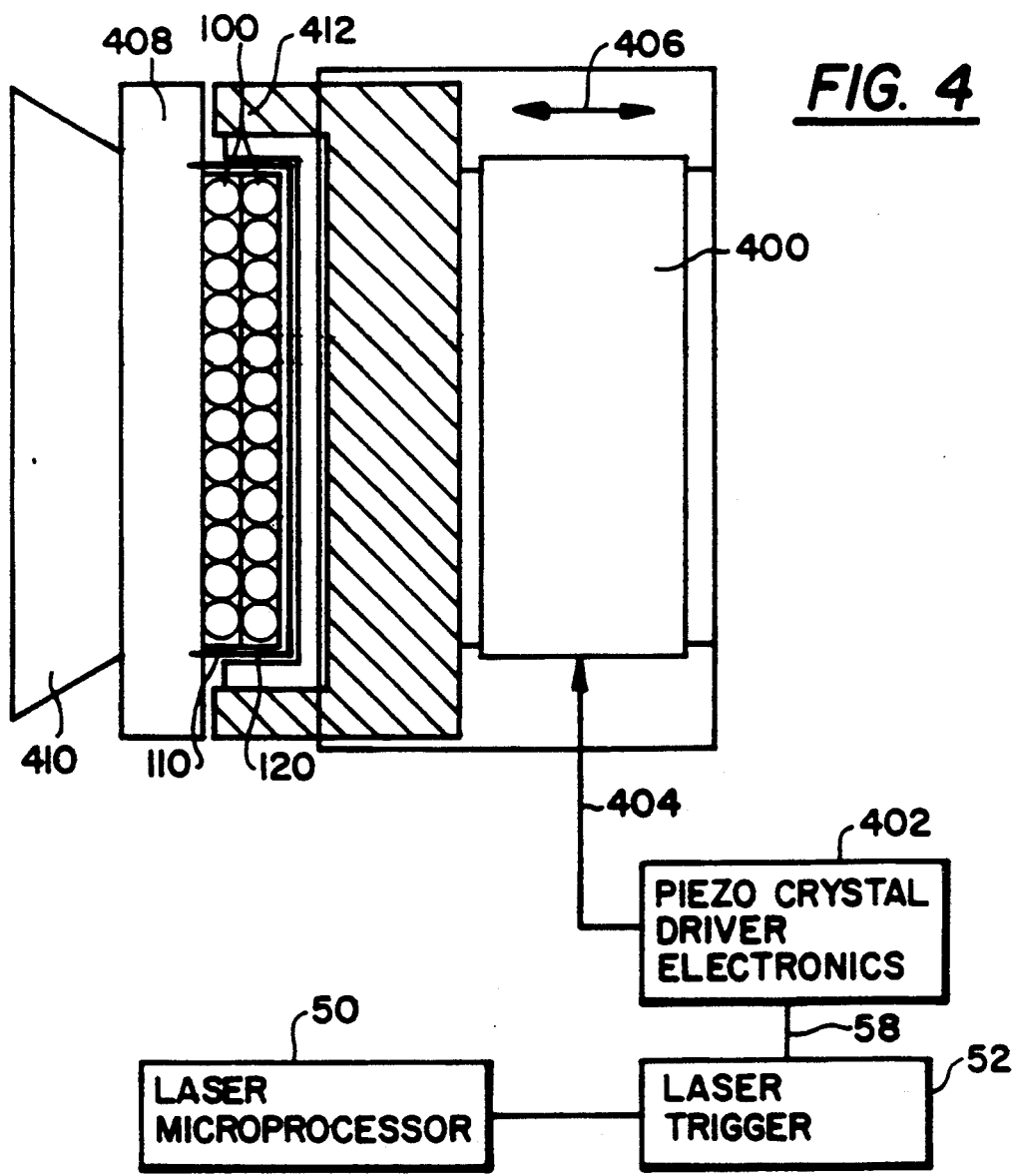

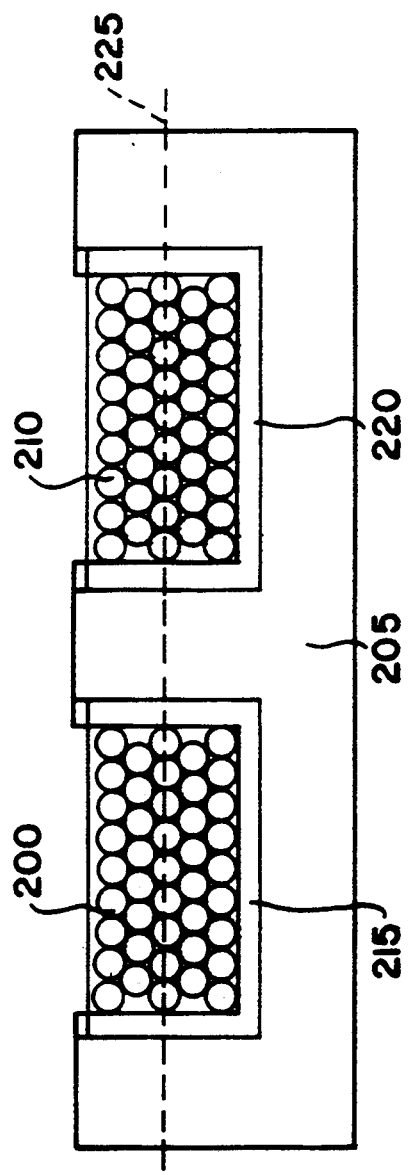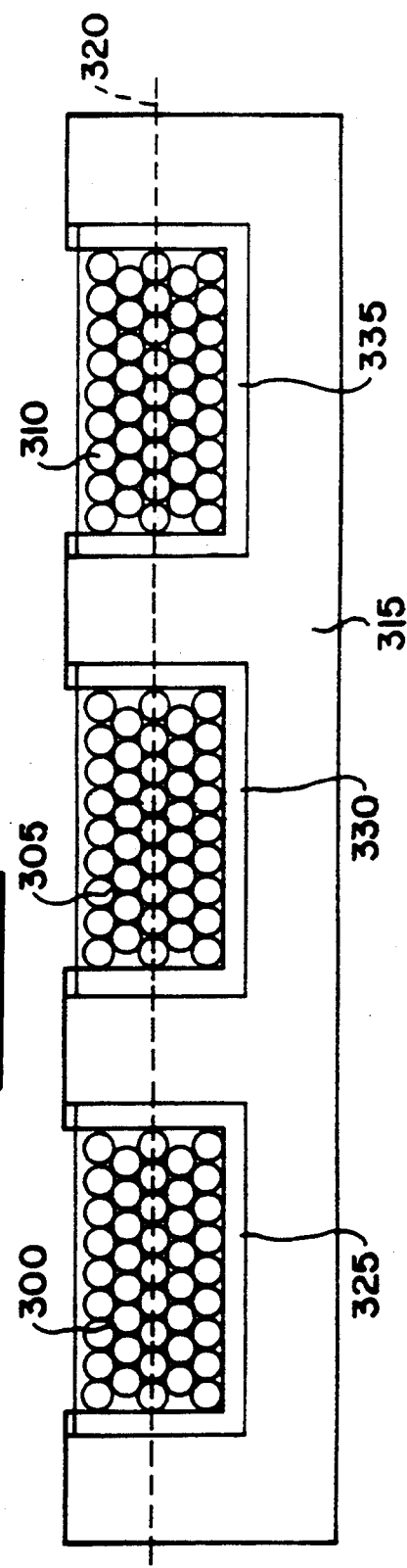

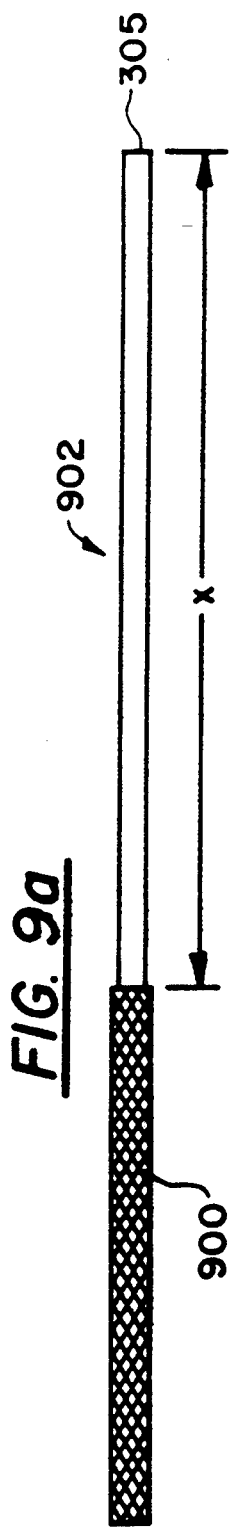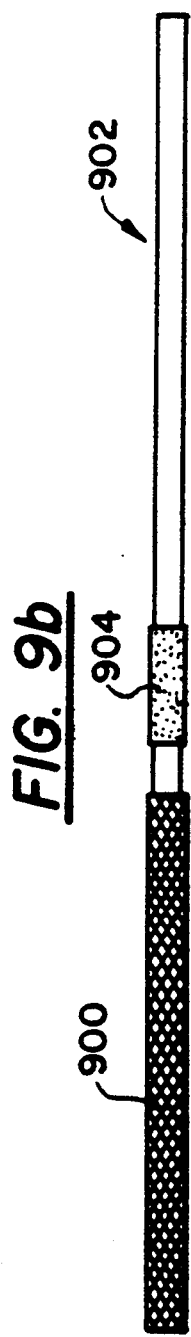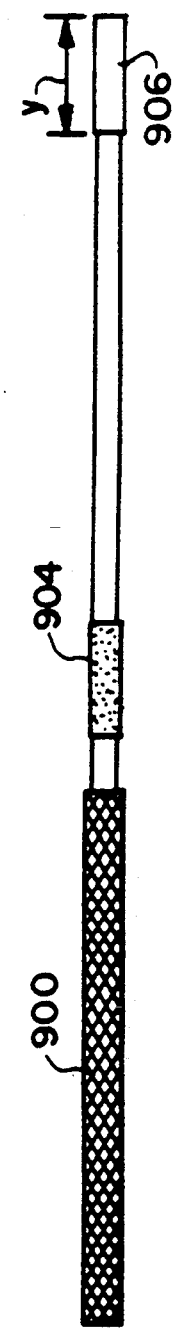

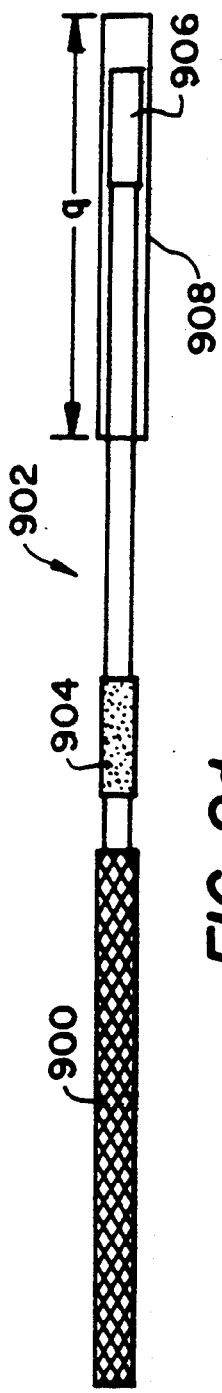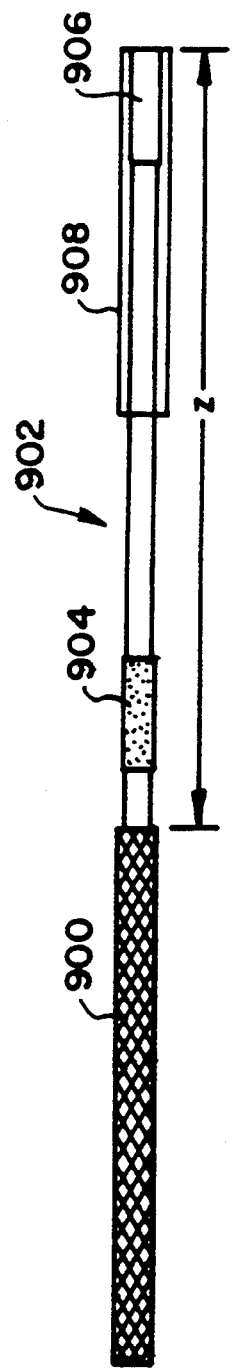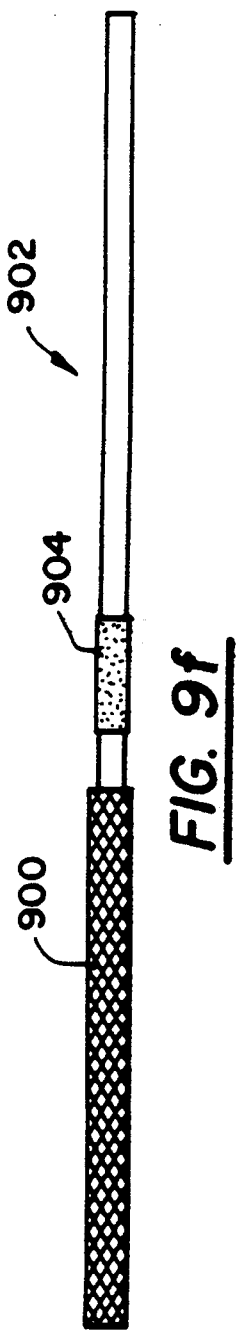

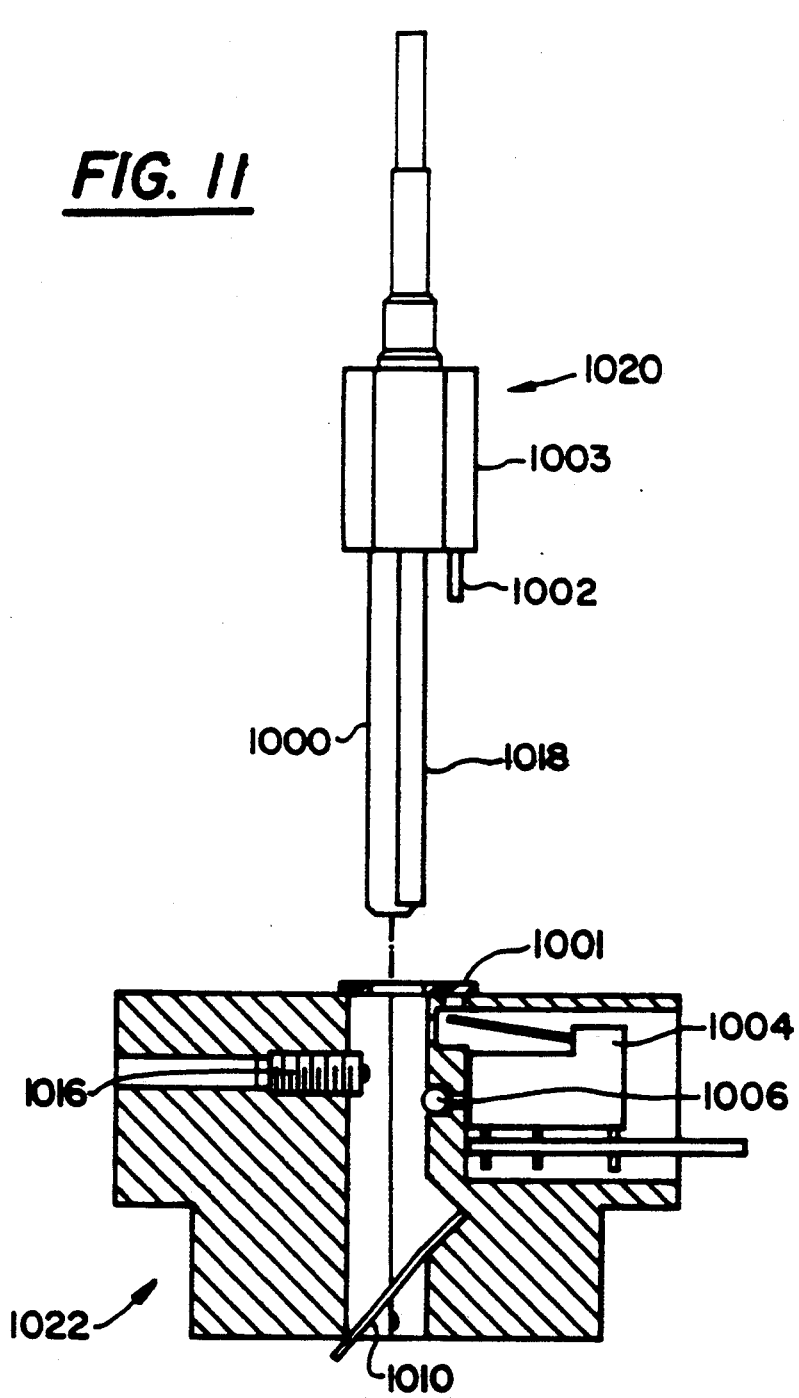

_5,400,428_

METHOD AND APPARATUS FOR LINEARLY SCANNING ENERGY OVER AN OPTICAL FIBER ARRAY AND COUPLER FOR COUPLING ENERGY TO THE OPTICAL FIBER ARRAY

CROSS REFERENCE TO RELATED APPLICATIONS

This is a continuation of application Ser. No. 07/882,597, filed on May 13, 1992, now abandoned, which was abandoned upon the filing hereof.

The subject matter of this application relates to U.S. patent application Ser. No. 07/417,245 issued as U.S. Pat. No. 5,016,964 entitled "Optical Fiber Coupler With Linear Input", the subject matter of which is incorporated herein by reference.

BACKGROUND OF THE INVENTION

1. Field of the Invention

This invention relates to a method and apparatus for linearly scanning an energy source over an array of optical fibers. More particularly, the present invention allows a series of energy pulses to be directed into different predetermined linearly-arranged segments of the optical fiber array.

2. Description of the Prior Art

The use of radiant energy sources, such as lasers, in medical procedures is presently attracting great attention. For several decades, scientists have described the use of lasers to ablate tissue. Suggested applications have included removing hair, corneal surgery, removing port wine stain and removing plaque from blood vessels. For example, percutaneous transluminal laser angioplasty involves the introduction of a catheter containing a bundle of optical fibers, into a blood vessel. The distal end of the catheter is positioned next to an obstruction in the blood vessel. Laser energy is applied to the optical fibers to ablate the obstruction. To be effective, each fiber in the bundle must carry laser energy having sufficient fluence (energy per unit area) to ablate tissue. Furthermore, laser surgeons have recognized the desirability of removing as large an area of the obstruction as possible without excessive manipulation of the catheter. This calls for a large number of optical fibers within the catheter. When laser radiation with a sufficiently high fluence is applied to a number of fibers simultaneously, a large amount of laser energy is introduced into the body. The body is traumatized by such energy. In fact healthy tissue can easily be damaged. At the same time, a large and costly laser is required to produce the large amount of energy.

Prior to this invention the seemingly contradictory goals of applying laser radiation of sufficient fluence over a relatively large area, while at the same time reducing the peak total energy applied to the body had not been realized.

Kittrell et al. U.S. Pat. No. 4,913,142 teaches a laser angioplasty system including a catheter housing a bundle of optical fibers. The multiple fibers allow the selection of tissue to be removed. Selectivity is achieved by monitoring spectroscopic characteristics. Each fiber of the bundle may be arranged in a linear array. Either the array or the laser energy is movable to allow each individual fiber to be selectively irradiated. First, low level energy is applied to each individual fiber in sequence and reflections from tissue proximate the distal end of the fiber are monitored to distinguish healthy tissue from tissue to be ablated. Then, high fluence laser energy is sequentially applied to one fiber at a time and only to those fibers illuminating tissue to be ablated. Nowhere in this patent is there any suggestion of the desirability or even the possibility of grouping more than one of the optical fibers making up the array for simultaneous irradiation. In fact, such an arrangement would destroy the fundamental function and purpose of the system described in the patent.

Alster U.S. Pat. No. 4,614,868 teaches an imaging system in which a laser beam can be scanned over a fiber optic bundle by irradiating fibers singly or in groups of fibers, the groups being as large as the spot size of the laser beam. However, this patent fails to suggest that scanning a laser beam, having sufficient fluence to ablate tissue, over a linear array of optical fibers is advantageous in reducing the total energy delivered or in reducing the size of the laser required.

Simon et al. U.S. Pat. No. 4,007,377 discloses an optical scanning system for use with universal product codes. A series of optical components, including a galvanometer, is used to expand the laser beam to illuminate an entire bar code. There is no suggestion of how a scanning system may be employed to maintain a sufficiently high fluence yet reduce energy in an ablation system.

Hotchkiss discloses, in U.S. Pat. No. 3,984,171, a linear scan system that provides a vertically and horizontally defined continuous linear scan of predetermined length. Even though Hotchkiss discloses a device that appears to be able to scan in a linear manner, there is certainly no suggestion to irradiate selected groups of optical fibers sequentially.

Chande U.S. Pat. No. 4,838,631 teaches a laser beam directing system for directing successive beam pulses of a pulsed laser into different optical fibers. This invention is especially useful with laser systems used in manufacturing and especially for use where a single laser is shared between several manufacturing workstations. There is no teaching that the device has any use in the medical field. This patent fails to suggest that scanning a laser beam, having a sufficient fluence to ablate tissue, over a linear array of optical fibers is advantageous in reducing the total energy delivered or in reducing the size of the laser required.

SUMMARY OF THE INVENTION

The present invention is directed at a more efficient apparatus and method of delivering energy to an optical fiber array. The optical fibers of the array are arranged to enable an energy source to sequentially irradiate different groups of fibers in the course of linear relative movement between the fibers and the energy. The present invention is extremely useful in medical applications, as the invention allows less energy per pulse (or the energy per unit time for a continuous wave (cw) energy source) to be delivered to a patient and the use of a less powerful energy source. In the present invention, not all of the optical fiber array is irradiated at one time. Therefore, the total energy per pulse (or the cw equivalent) delivered to the patient can be reduced. The irradiated portion of the optical fiber array, while still maintaining a fluence level in each fiber of the portion sufficient to ablate tissue, receives and transmits less energy per pulse to the tissue upon which surgery is being performed than if all fibers in the array are irradiated simultaneously, thus reducing the risk of injury to the patient. In medical applications, the system alleviates much of the concern involved with delivering large quantities of energy to human tissue in a single pulse.

The present invention relies upon "multiplex coupling" to couple energy to an array of optical fibers. Because not all the fibers in the array are irradiated simultaneously, the fiber area used in the fluence calculation is smaller. To compensate for the decrease in area, the energy per pulse can be reduced, thus yielding the same fluence as when all fibers are irradiated at a higher energy per pulse. In this manner, less laser energy per pulse is delivered to the patient.

Although the present invention is applicable for use with a wide array of energy sources, the preferred embodiment uses a linearly focused laser beam to provide a substantially uniform distribution of energy over the optical fiber portion that is irradiated. That is, all fibers in the portion experience the same modal excitation as a result of using the linearly focused laser beam.

According to the preferred embodiment of the present invention, portions of a fiber array are sequentially irradiated with each laser pulse. That is, the laser beam can be linearly scanned across the array and irradiate ¼, ⅓ or ½ of the optical fibers of the array in each pulse. Of course, the fraction of the optical fibers is not limited to ¼, ⅓ or ½, but may be any fraction so long as the number of fibers illuminated is greater than one but less than the total number of fibers.

One embodiment of the array includes a single row of optical fibers. As described above, the incident laser beam may irradiate ½, ⅓, ¼, etc. of the fibers with successive pulses.

The array may be more than a single row of optical fibers. For example, the array could be two parallel rows of optical fibers. Either sequential portions of both rows of fibers can be illuminated or either the first row and then the second row can be illuminated by the laser light.

Another possible array configuration is to have a plurality of bundled fibers, where each bundle is the same size, disposed along a common transverse axis. Each bundles is composed of more than one optical fiber. Further, each bundle makes up, for example, ½, ⅓, ¼, etc. of the total number of optical fibers. The present invention operates by irradiating successive bundles of fibers.

As the present invention only illuminates a fraction of a fiber array with each pulse of energy, the invention thus allows for a reduction in the energy per pulse (or the cw equivalent) delivered to a patient and a reduction in the size of the energy source. Hence, it is an object of the present invention to reduce the energy per pulse (or the cw equivalent) and size of the energy source by providing a linear optical scan system for an energy source.

Furthermore, the present invention may employ a quick coupling system particularly suited to the scanning arrangement of the present invention.

BRIEF DESCRIPTION OF THE DRAWINGS

Other objects, features and characteristics of the present invention, as well as the methods of operation and function of the related elements, will become apparent upon consideration of the following description and the appended claims with reference to the accompanying drawings, all of which form a part of this specification. In the drawings, like reference numerals designate corresponding parts in the various figures, of which:

FIG. 1 is a schematic diagram of one embodiment of the present invention;

FIG. 2 is an enlarged view of a fiber bundle across which the laser beam is scanned;

FIG. 3a is an enlarged view of a second embodiment of the fiber array in a first scan position;

FIG. 3b is an enlarged view of the second embodiment in a second scan position;

FIG. 4 depicts apparatus for implementing the scanning in FIGS. 3a and 3b;

FIG. 5a depicts another embodiment of the fiber array;

FIG. 5b shows yet another embodiment of the fiber array used in conjunction with the present invention;

FIG. 11 illustrates the same device as pictured in FIG. 10, with the male and female coupling portions separated.

DETAILED DESCRIPTION OF THE PRESENTLY PREFERRED EXEMPLARY EMBODIMENTS

Figure 6:
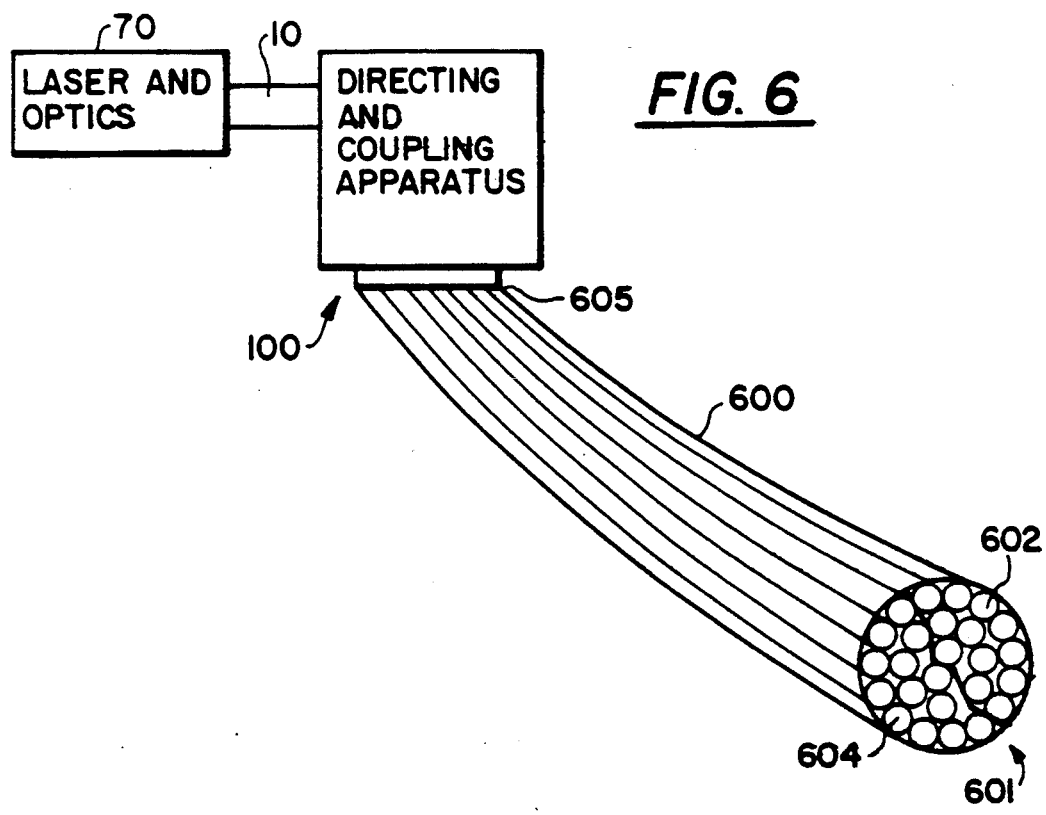
FIG. 6 illustrates the present invention utilized in a laser catheter.

FIG. 1 is a schematic diagram of the present invention. Energy, such as laser beam 10, preferably produced by an excimer laser, is focused by a lens system so as to be linear in cross section. The laser and optics assembly is shown generally at 70 and is described in detail in U.S. Pat. No. 5,016,964. Of course, laser beam 10 could be produced by a laser other than an excimer laser. In fact, the energy could be generated by a source other than a laser.

The linearly focused beam 10 enters focusing/guiding apparatus 14 at position 11 and is incident on dielectric mirror 13 disposed on scanner 12. The exact dielectric coating used to form mirror 13 varies depending on the laser radiation employed. That is, the dielectric mirror 13 is chosen so as to optimize reflection for the particular wavelength of laser energy that is employed. Scanner 12 is preferably a stepper motor that moves mirror 13 between positions. Alternatively, scanner 12 may be a galvanometer or a linear translator driven by a motor, cam or piezo crystal stack. A galvanometer may provide improved accuracy and scanning speed.

Scanner 12 rotates mirror 13 as indicated by arrow 15. Although arrow 15 appears to indicate significant deflection, the amount mirror 13 is deflected is in reality very minute. The deflection of mirror 13 is only enough to scan laser beam 10 over fiber optic array 20. Scanner 12 moves laser beam 10 in the direction indicated by arrow 21. It is equally possible to move the fiber array rather than laser beam. Such a system will be discussed with reference to FIG. 4.

Optical elements 16 and 18 are interposed in apparatus 14 between scanner 12 and array 20. Elements 16 and 18 may be devices such as lenses or filters. Lenses are used to adjust the size of the linearly focused beam 10.

The normal or rest position of beam 10 is indicated by reference numeral 28 in FIGS. 1 and 2. That is, if the laser beam was not scanned over fiberoptic array 20, beam 10 would land on and irradiate position 28. Side sections 25 and 27 are juxtaposed to normal position 28 of beam 10. Fiber array 20 may thus be broken into three distinct sections when beam 10 is not being scanned thereacross. These sections are the normal position 28 of beam 10 and the two side sections 25 and 27.

A first embodiment of the invention will be described in connection with what is one possible manner in which scanning of beam 10 over array 20 can be accomplished. The first embodiment is directed at an arrangement in which laser energy is moved between two scanning positions. That is, array 20 is scanned in sections equivalent to half the array.

Beam 10 is scanned across fiberoptic array 20 as is suggested by arrow 21 indicating the direction of scanning. Array 20 is composed of a plurality of optical fibers 22, all of which are of uniform diameter D. Scanner 12 moves dielectric mirror 13 so that beam 10 is displaced from its normal position 28 to a first scan position 24 to cover half of the optical fibers, from one end of linear array 20. The laser pulse from the laser irradiates the optical fibers encompassed by the first scan position. In this embodiment, first scan position 24 includes those fibers within side section 25 and half of the fibers falling within normal position 28.

Thus, the first pulse from excimer laser/linear focusing optics 70 irradiates half of the linear array 20. Of course, as suggested earlier, the first pulse may irradiate ⅓ or ¼ or any other fraction of the fiberoptic array. The pulse is not scanned on a fiber by fiber basis, but rather each pulse irradiates at least two optical fibers 22. In the embodiment depicted in the drawings, each pulse irradiates approximately twelve optical fiber. If the first pulse from laser and optics assembly 70 was intended to irradiate ⅓ of array 20, then only eight optical fibers would be illuminated by each pulse. When only ¼ of the linear array is illuminated with each pulse, then in the pictured embodiment, six fibers would be illuminated by each pulse as the beam is scanned over array 20.

After the laser pulse from the excimer laser is directed to those optical fibers falling within first scan position 24, scanner 12 moves dielectric mirror 13 so as to direct the next laser pulse to second scan position 26. Second scan position 26, in this embodiment, encompasses the fibers not falling within first scan position 24. That is, the second scan position 26 includes the second half of the linear fiber optic array 20 including fibers within side section 27 and half of the fibers within normal position 28. As described above, fiber optic array 20 could be scanned in a manner other than by half per pulse. If this were the case, the second pulse from laser and optics assembly 70 could be directed at the second third, second quarter, etc. of array 20.

The ability of the present invention to scan the energy source over array 20 enables a reduction in the energy per pulse (or the cw equivalent) supplied to the patient and therefore the size of the energy source. Further, since more than a single fiber is being irradiated with each excimer laser pulse, the optics needed to focus pulsed beam 10 are simple as can be seen in U.S. Pat. No. 5,016,964.

An array of optical fibers such as that described above is formed by the following process. First, the optical fibers are cut with, for example, a cutting stone. The cut end is then cleaned with alcohol. The fibers are then sorted into as many bundles as there are groups of fibers to be irradiated. For example, if half the array of optical fibers is irradiated with each pulse, the fibers would be sorted into two groups. A piece of shrink tubing is then placed over the bundle. The fiber bundle is then inserted into the handle of the male plug portion (to be described with reference to FIGS. 10 and 11). At least one inch of the plastic coating covering the fibers is then stripped off the fibers using a furnace set between 600° C. and 800° C. The fiber bundle is then placed on a substrate of a male coupling portion will be described. The bare fibers should extend past the end of the substrate and stick out by about 25 mm. A portion of covering the fibers extends onto the substrate. A curable adhesive, such as NORLAND 123 UV, is applied to the tubing so as to couple the tubing to the substrate, being careful not to apply an adhesive to the fibers. The adhesive is then cured under UV light.

The fibers are then spread into a single row on the substrate. It is important that the fibers be maintained in their respective groups that they were sorted into earlier. This is done by using a distal spreading apparatus adjacent the substrate to maintain a space between adjacent groups of fibers. The distal spreading apparatus abuts the substrate and includes a ridge or projection disposed thereon, running parallel to the fibers, to maintain the separation of the overhanging fibers. It is desirable not to irradiate the end fiber(s) of each group by successive pulses of the laser beam, and this is ensured by spacing the groups of fibers on the substrate.

Once the fibers are spread across the substrate, a needle or other aid is used to straighten the fibers. Adhesive is then applied to the fibers. For example, one drop of NORLAND 81 is applied to Catheters having less than 25 fibers while two drops are used for catheters having more than 25 fibers. The adhesive is then gently spread over the fibers. Once any bubbles that might have formed in the adhesive are removed, the adhesive is cured using UV light. The overhanging fibers are then cleaved near the substrate. The fibers are then polished.

Another embodiment of a fiber array that may be used is pictured in FIGS. 3a and 3b. FIGS. 3a and 3b depict 2×12 linear array of optical fibers 100. Certainly, the array can be scanned in two or more segments (2×6, if two segments are assumed) in the manner described with respect to FIGS. 1 and 2 above. The energy source would simply be less tightly focused to simultaneously irradiate two rows of fibers. Alternatively, as illustrated in FIGS. 3a and 3b, the first laser pulse may be focused on part of the array 110 that is 1×12 in size and then the apparatus directs the second pulse at remaining fibers 120 that are also dimensioned 1×12. Of course, more than two rows of fibers may be provided and the rows of fibers may include a fewer or a greater number of optical fibers than the 12 pictured in FIGS. 3a and 3b.

To accomplish the scanning in the embodiment of FIGS. 3a and 3b, either the beam deflection can be shifted using equipment similar to that illustrated and described with respect to FIG. 1. Alternatively, the fiber array can be shifted as illustrated in FIG. 4.

FIG. 4 illustrates an apparatus for translating the fiber array for irradiating different portions of optical fiber array 100. Piezo crystal stack 400 expands and contracts, as indicated by arrow 406, in response to signal 404 sent from piezo crystal driver electronics 402. Piezo crystal driver electronics 402 is controlled by signal 58 from laser trigger 52, which in turn is controlled by laser microprocessor 50. Laser microprocessor 50 and laser trigger 52 are described further with respect to FIG. 7.

Stacked optical fiber array 100 is secured to fiber mounting substrate/coupler body 408. In turn, fiber mounting substrate 408 may be secured to an element such as spring steel counter 410, which permits movement of the stacked fiber array 100 as piezo crystal stack 400 expands and contracts. Translator reference surface 412 is provided for proper alignment of optical fiber array 100 so that portions of fiber array 110 and 120 are sequentially irradiated.

The first pulse generated by laser 70 (FIG. 1) irradiates part of optical fiber array 110 pictured in FIG. 3a. The piezo crystal stack then expands so that part of optical fiber array 120, as pictured in FIG. 3b, is irradiated. Note that in FIG. 4, portions 110 and 120 contain only eight fibers apiece rather than the twelve depicted in FIGS. 3a and 3b.

Additional embodiments of the array of optical fibers are shown in FIGS. 5a and 5b. FIG. 5a illustrates a grooved fiber holder 205 holding two equally sized bundles of fibers 200 and 210. Bundles 200 and 210 are centered upon the same linear transverse axis 225. The laser beam is focused so that the first incident beam pulse 215 irradiates all of fiber bundle 200, which is half of the total fibers. Either the beam or the fibers are then shifted so that next pulse 220 of the laser beam is focused on bundle 210.

FIG. 5b illustrates three bundles of optical fibers 300, 305 and 310. Each bundle of fibers 300, 305 and 310 contains ⅓ of the total number of fibers. The optical fiber bundles are disposed in a grooved fiber holder 315. First scan position 325 irradiates fiber bundle 300. The beam and fibers move relative to one another to irradiate fiber bundle 305. The next laser pulse is directed at third bundle of optical fibers 310, which fall in third scan position 335. As in FIG. 5a, the fiber bundles are disposed in a linear manner along the same transverse axis 320 to provide for linear scanning.

Figure 8A:
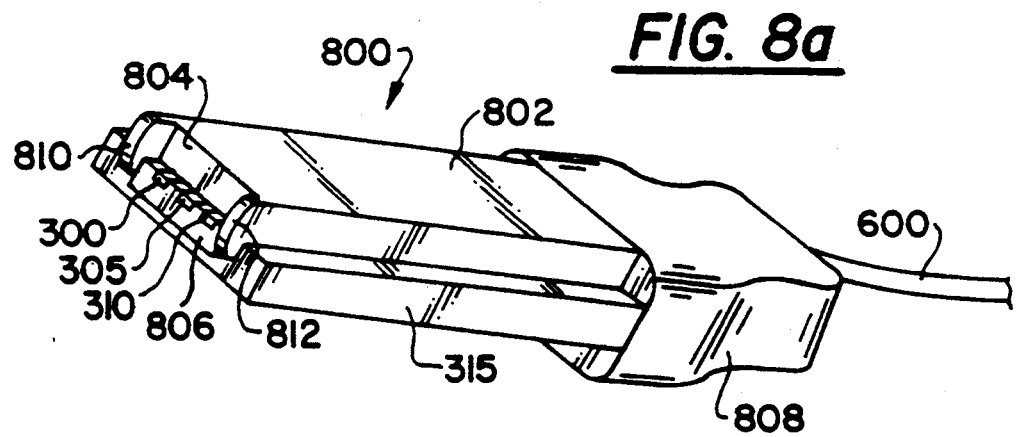
FIGS. 8a and 8b illustrate a perspective and front view of the male coupler according to the present invention.
Figure 8B:
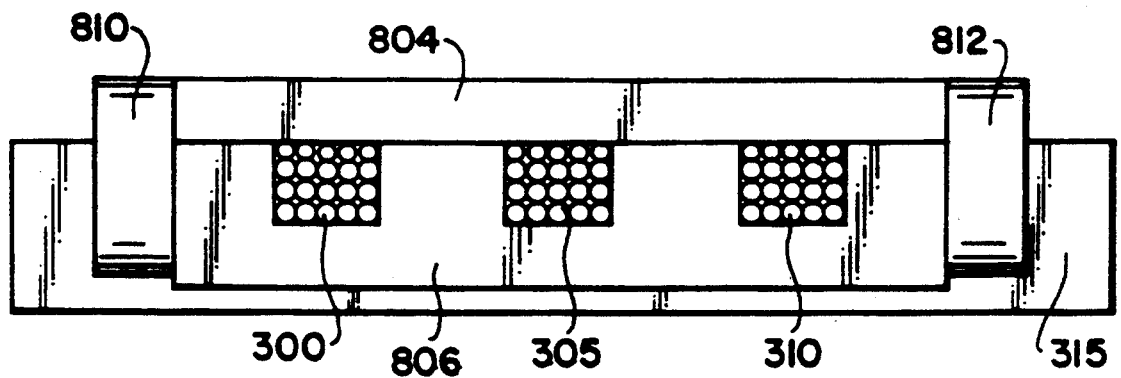

FIGS. 8a and 8b illustrate plug portion 800 of a laser catheter having an array of optical fibers whose proximal end are disposed as depicted in FIG. 5b. Grooved fiber holder 315 is, for example, a plastic substrate having three grooves formed therein. Fiber bundles 300, 305 and 310 are disposed in the grooves in fiber holder 315. Fiber holder 315 includes an inclined proximal face 806. Inclined face 806 slopes inward from the bottom surface of fiber holder 315 in the direction of plug handle 808.

Plug portion 800 also includes an upper plate 802. Upper plate 802 is preferably formed of molded plastic and is connected to fiber holder 315 via connecting members 810, 812, which are formed integral with upper plate 802. Like fiber holder 315, upper plate 802 includes an inclined face, specifically inclined face 804. Inclined face 804 slopes inward from the top surface of upper plate 802 in the direction of plug handle 808.

Inclined faces 804 and 806 allow for the fiber bundles to overhang from fiber holder 315 and upper plate 802. It is also possible for faces 804 and 806 to be cut back from the rest of upper plate 802 and fiber holder 315. The main goal is to allow for the optical fibers to extend past the edge of the fiber holder 315 and the upper plate 802. Such an overhang as pictured in FIG. 9j enhances the durability of the fibers by preventing input surface contamination, which can be caused by ablation by-products of the mounting substrate.

Within plug portion 800, fiber bundles 300, 305 and 310 are joined into a single bundle that exits plug portion 800 as catheter 600, explained below with reference to FIG. 6.

Figure 9G:
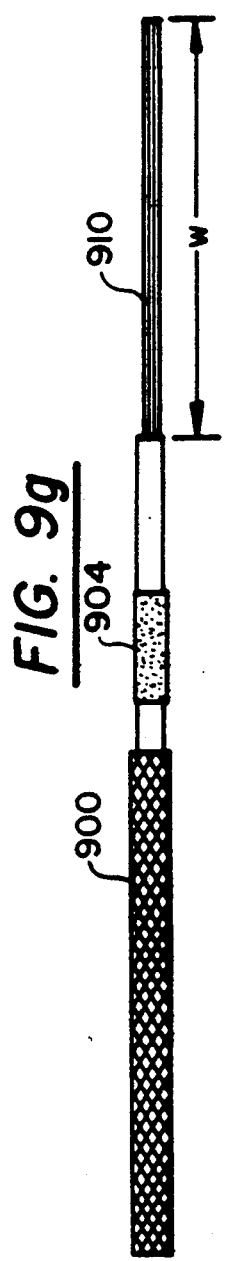
FIGS. 9a–9o illustrate the process for positioning fiber bundles into grooves.
Figure 9H:
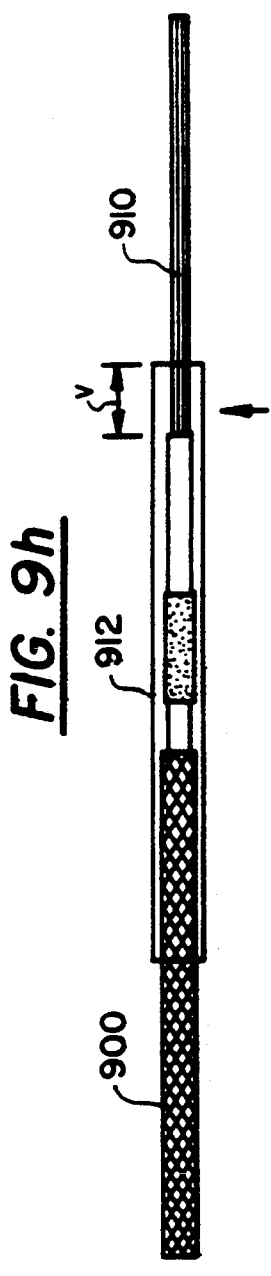
Figure 9I:
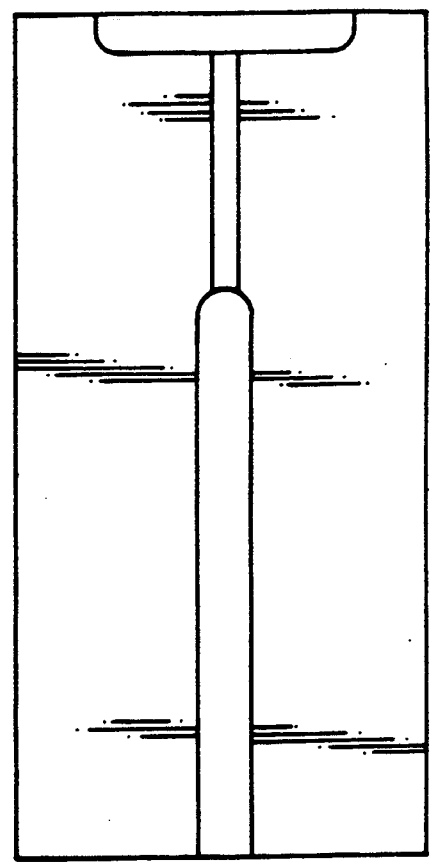
Figure 9J:
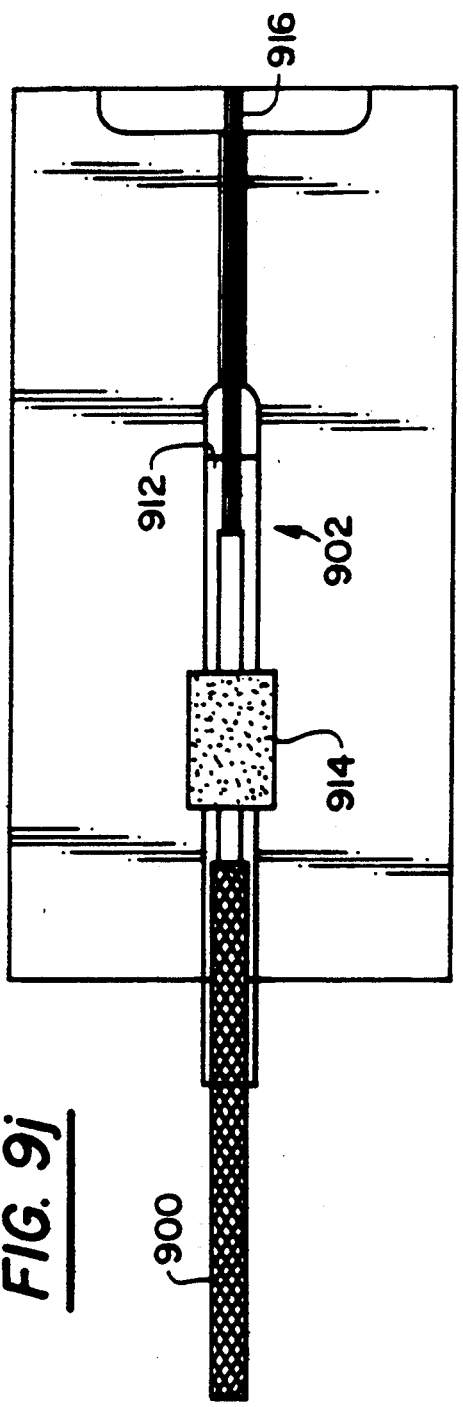
Figure 9K:
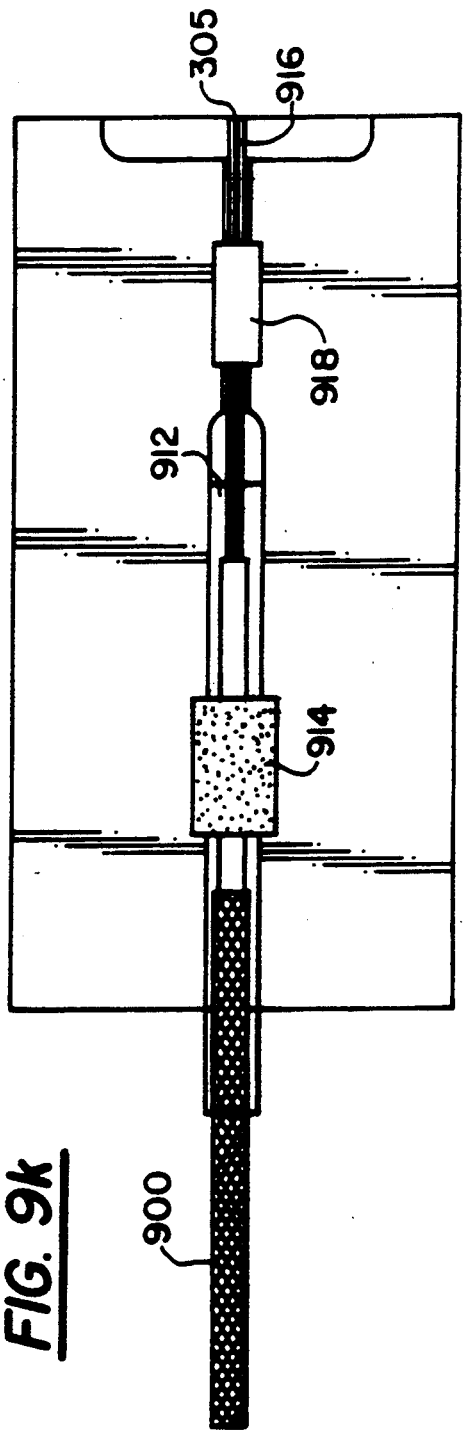
Figure 9L:
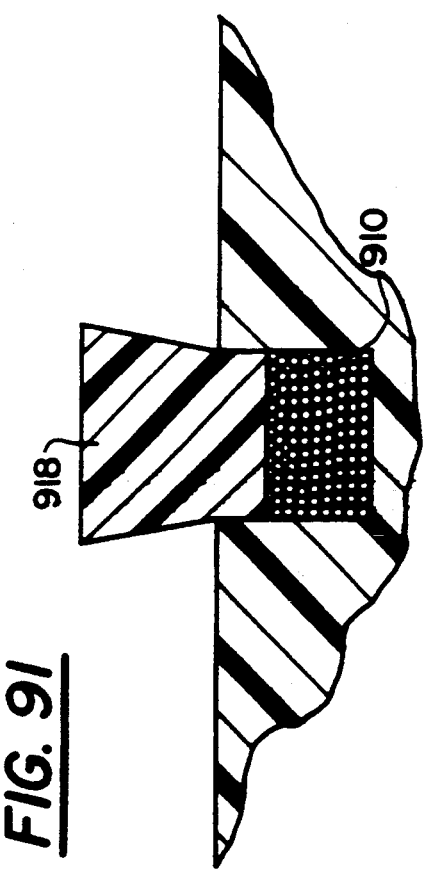
Figure 9M:
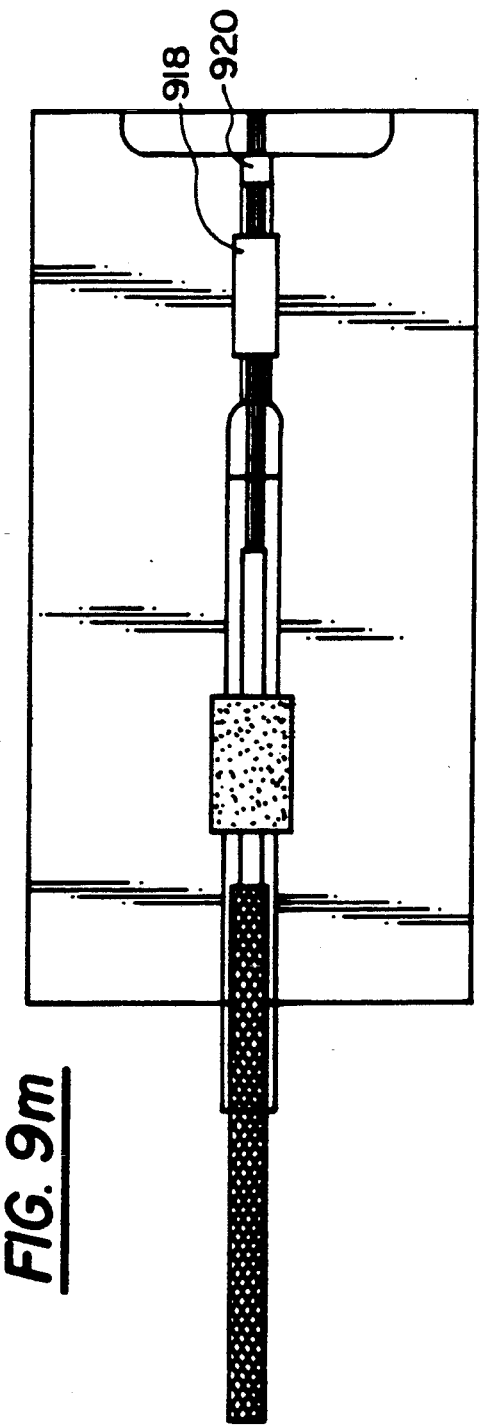
Figure 9N:
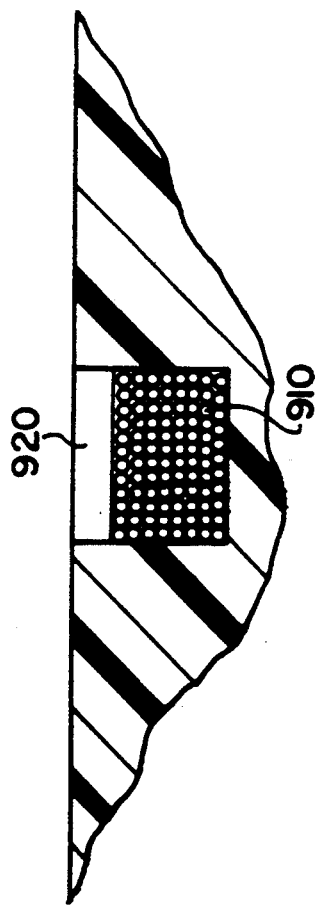
Figure 9O:
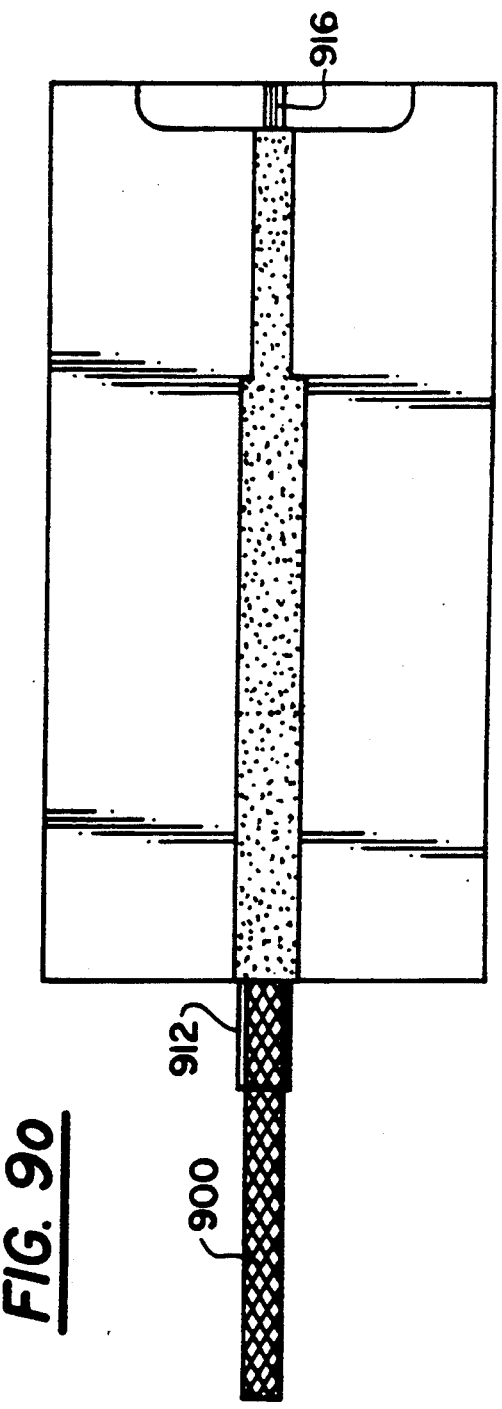

FIGS. 9a–9o depict the method of laying a fiber bundle into one groove on a fiber holder. Such a method is utilized for each bundle held by the fiber holder.

FIG. 9a illustrates tail tubing 900 being pulled back from optical fiber bundle 902 so as to expose length "x", approximately equal to 1.875 to 2 inches, of fibers 305. In FIG. 9b, a glue plug 904 is formed just below the end of tubing 900. Glue plug 904 is formed of a fast drying epoxy.

Crystal bond, or a similar potting material, 906 is applied to length y, measuring about 0.25 to 0.375 inches, along the bare fibers as shown in FIG. 9c. A heat gun or hot box (not pictured) is then used to melt the crystal bond and heat the ends of the fibers. This allows crystal bond 906 to work in between the fibers to ensure good support during polishing. As pictured in FIG. 9d, length q of shrink tubing 908 is shrunk over the potted area and fibers to provide extra support during polishing. Length q measures about 0.75 inches.

Utilizing a diamond wire saw (not pictured), the tip of optical fiber bundle 902 is cut such that crystal bond, or like potting material, 906 is trimmed as shown in FIG. 9e. Length z of optical fiber bundle 902 remains exposed, with length z being about 1.75 inches. The tip of optical fiber bundle 902 is then polished, by a device such as a BUEHLER polishing machine (not shown), using 12, 3 and 0.3 micron lapping paper. Polishing is continued until all chips are gone and all fibers appear to have an optical quality polish.

Shrink tubing 908 is then removed from optical fiber bundle 902. This is done by placing the potted end in heat and sliding the shrink tubing off. The polished end of optical fiber bundle 902 is then suspended in acetone and placed in ultrasonic cleaner so as to remove completely crystal bond, or other potting material, 906. Care must be taken not to damage or chip the polished fibers as the potting material 906 is removed from the end of optical fiber bundle 902. This step is depicted with reference to FIG. 9f.

Polyimide is then stripped off length w of fiber ends by placing the optical fiber bundle in a tube furnace (not shown) at a temperature of about 780° F. for 1.5 minutes. Thus, exposed fibers 910 are left. These must be handled quite carefully, since the fibers are quite fragile. Length w is approximately equal to 1 inch. FIG. 9g illustrates this step.

In FIG. 9h, an approximately 1.25 inch piece of shrink tubing 912 is positioned so that it overlaps the stripped portion of fibers by length v, which is about 0.125 inches. Shrink tubing 912 is then shrunk. Still, care must be taken when manipulating exposed fibers 910 as they remain fragile.

FIG. 9i illustrates the mounting slide upon which the optical fiber bundle is to be disposed. For the purpose of inserting optical fiber bundles 300, 305 and 310 onto a slide with three grooves, this process is repeated three times.

FIG. 9j illustrates the insertion of fibers into the groove on the slide. Optical fiber bundle 902 is positioned in the groove so that the ends of the polished fibers are flush with the end of the slide. Tip 916 of optical fiber bundle 902 projects past the end of the groove. Such a structure enhances the durability of the fibers by preventing input surface contamination, which can be caused by ablation by-products of the mounting substrate. Wetting the fibers with purified water makes it easier to insert optical fiber bundle 902 into the groove. Quartz-filled ultraviolet cure adhesive 914 tacks the fibers to the slide.

As pictured in FIGS. 9k and 9l, pressure is applied to wetted fibers 910 using a silicone or rubber wedge 918. While observing with a microscope (not pictured), tip 916, which still has wet optical fibers, is probed and manipulated, carefully and gently, so that fibers 305 are positioned into a rectangular close pack.

FIGS. 9m and 9n illustrate how fibers 910 are tacked into the groove. While pressure is maintained using the silicone or rubber wedge 918, tack 920 is placed on exposed fibers 910. This step is performed while the fibers 910 are still wet. It is desirable not to disturb the packing of fibers 910. Finally, in FIG. 9o, the entire grooved fiber assembly is potted, thus allowing the fibers to remain positioned in the groove. The same procedure described with reference to FIGS. 9a–9o is followed for all other fiber bundles to be disposed on a slide.

FIG. 6 illustrates the present invention used in a laser catheter assembly. Laser 70 generates beam 10, which is transmitted to directing and coupling apparatus which implements either the apparatus of FIG. 1 or FIG. 4. Laser beam 10 enters catheter 600 from the directing and coupling apparatus. Proximal end 605 of catheter 600 connects to the directing and coupling apparatus. Proximal end 605 may be shaped as a stacked fiber array as shown in FIGS. 3a and 3b. Of course, proximal end 605 may also be in the form of fiber array discussed with respect to FIGS. 5a and 5b.

The stacked fiber array at the proximal end of any of the forms described above turns into a substantially circular fiber bundle for use as a catheter. Distal end 601 of catheter 600 is substantially circular and is inserted into the patient.

In the assembly process, the fibers are sorted so that adjacent fibers at distal end 601 are irradiated simultaneously. Thus, for a fiber array at the proximal end that is irradiated in two portions, the fibers of one portion form portion 602. Likewise, fibers of the other portion become portion 604 at distal end 601 of catheter 600.

Figure 7:
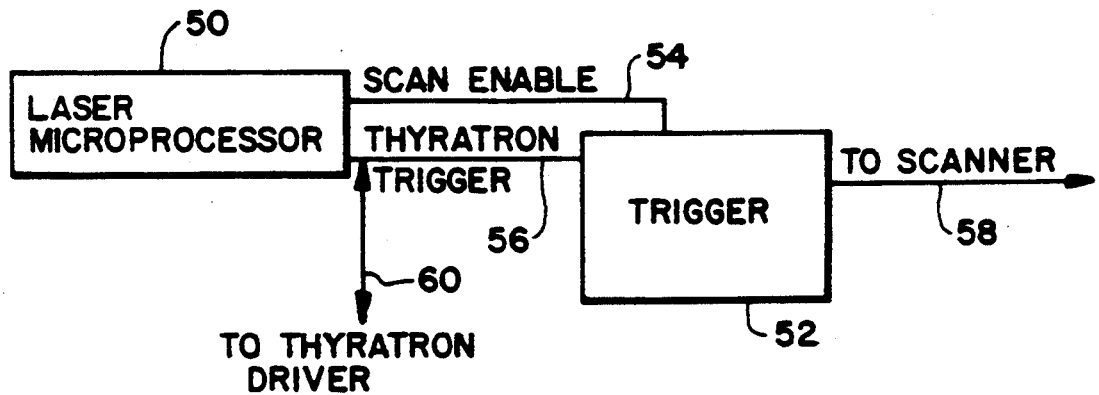
FIG. 7 schematically illustrates control apparatus of the scanners pictured in FIGS. 1 and 4.

Control of scanner 12 in FIG. 1 will now be explained with reference to FIG. 7. Laser microprocessor 50 communicates with trigger circuit 52 via signals 54 and 56. Signal 54 is a scan enable signal which indicates that the laser system is operational and that scanning is desired. When the laser is to be fired, microprocessor 50 generates thyratron trigger signal 56 to cause a thyratron in the laser drive circuit to conduct, triggering the laser. While scan enable signal 54 is enabled, after the laser has fired, trigger circuit 52 generates a signal on line 58 which causes scanner 12 or piezo electric stack 400 to move so that the next portion of fibers will be irradiated with the next firing of the laser. The signal on line 58 is, for example, a square wave that incrementally moves scanner 12.

Trigger circuit 52 may include a D flip-flop that receives scan enable signal 54 as an enabling signal and thyratron trigger signal 56 as a clock signal. The output of the flip-flop may be amplified before being applied to scanner 12 or piezo electric stack 400. In the preferred embodiment, scan enable signal 54 remains at a continuous level during scanning. During ablation, thyratron trigger signal 56 periodically triggers a laser pulse. After each laser pulse, scanner 12 or piezo electric stack 400 is actuated so that the next portion of fibers will be irradiated with the next laser pulse.

Figure 10:
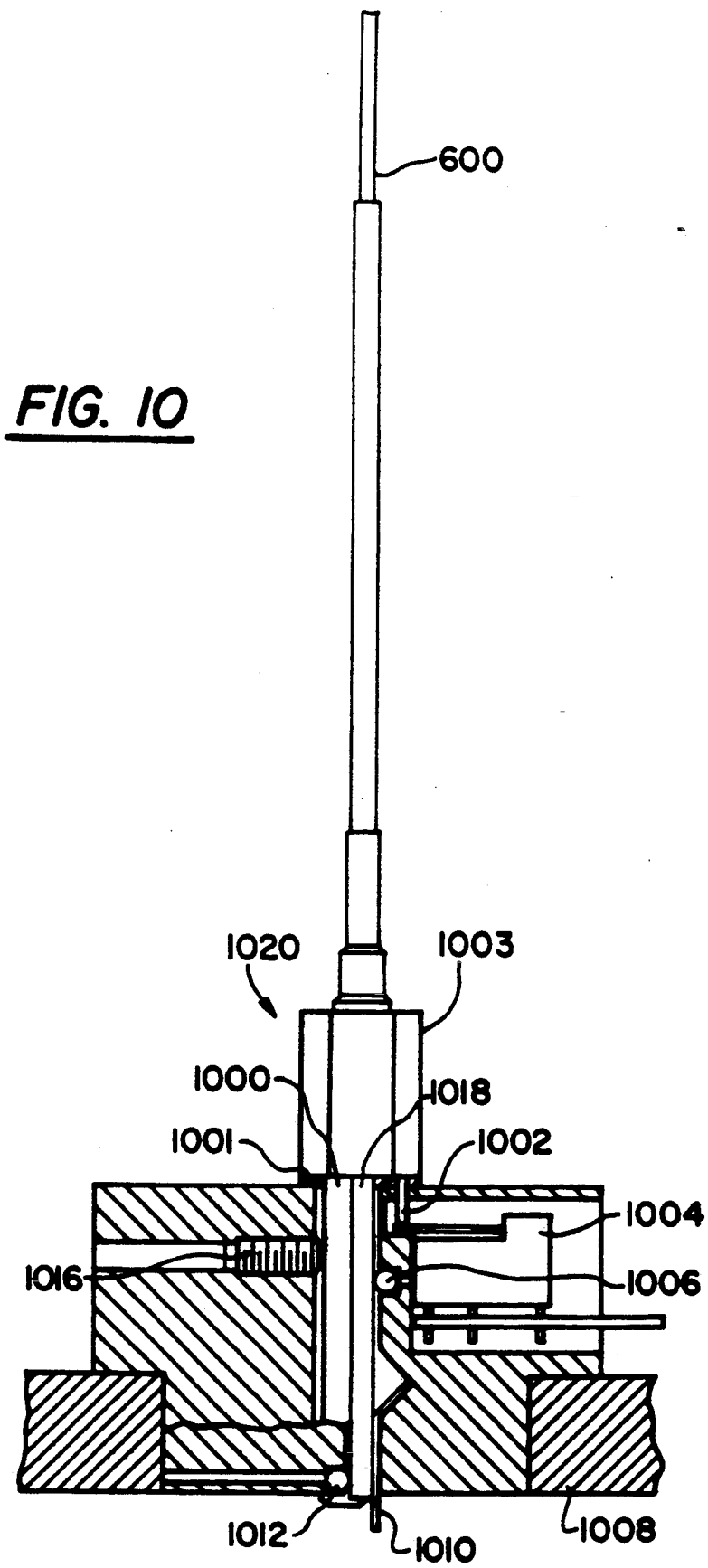
FIG. 10 illustrates an optical fiber coupler including a male coupling portion and a female coupling portion particularly suited for use with the present invention.

A mechanism particularly well suited for use in a scanning system is depicted in FIGS. 10 and 11, where fiberoptic catheter 600 is attached to male coupling portion 1020. Male coupling portion 1020 includes handle member 1003, slide 1000 and base substrate 1018. Handle member 1003 allows easy handling as well as preventing any extraneous laser radiation from being emitted. Optical fibers are disposed between slide 1000 and base substrate 1018. Substrate 1018 may hold array 20 of FIG. 2, array 100 of FIG. 3 or be holder 205 or 315 of FIG. 5a or 5b, respectively.

Male coupling portion 1020 attaches to female coupling portion 1022. Female coupling portion 1022 receives male coupling portion 1020 in a groove or aperture formed therein. The shape of the groove or aperture is such that slide 1000 and substrate 1018 fit snugly therein. Keying pin 1002 provided on male coupling portion 1020 is used to identify the size of fiberoptic catheter 600. Pins 1002 come into contact with micro switches 1004 disposed in female coupling portion 1022. The manner in which pins 1002 contact switches 1004 controls the unique signal generated by micro switches 1004. Between male and female coupling portions 1020 and 1022 is compressible foam member 1001, which prevents leakage of laser radiation when male coupling portion 1020 is inserted into female coupling portion 1022.

Male coupling portion 1020 is held in place in female coupling portion 1022 by spring plunger 1016 and reference balls 1006 and 1012. Spring plunger 1016 provides pressure to seat coupler on back reference ball 1006 and locks male coupling portion 1020 in female coupling portion 1022 when spring plunger 1016 drops into a v-groove (not shown) formed in slide 1000. Reference ball 1006 guides the protruding portion of the male coupling portion 1020 into the receiving groove or aperture in female coupling portion 1022. Reference ball 1012 provides repeatability by pressing the substrate 1018 with optical fibers disposed thereon into a position such that the fibers are illuminated by the laser radiation. Spring steel shutter 1010 provides pressure on the back of the substrate 1018 so that reference ball 1012 is seated appropriately. Further, spring steel shutter 1010 blocks the laser beam when male coupling portion 1020 is removed from female coupling portion 1022.

Female coupling portion 1022 connects to laser and optics assembly (not shown) via use of mounting plate 1008. The mounting plate and female coupling portion 1022 are slip fit so that the coupler may be rotated to correct or improve alignment. While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An apparatus for ablating tissue comprising:
a pulsed energy source;
means for focusing said energy;

a bundle of optical fibers, a proximal end of said fibers being disposed in an array;

means for directing said focused energy on a group of at least two and less than all of said fibers; and linear scanning means for causing said directing means to sequentially direct said focused energy on different groups of said optical fibers;

wherein said optical fibers receive less energy than is necessary to produce a fluence in all the fibers simultaneously to ablate tissue; and wherein said directing means directs said individual pulses of said energy so that each fiber of the group irradiated outputs radiation having a sufficiently high fluence to ablate tissue.

2. An apparatus for ablating tissue as claimed in claim 1, wherein:

said producing means includes means for producing a pulsed laser beam.

3. An apparatus for ablating tissue as claimed in claim 1, wherein said directing means includes a mirror.

4. An apparatus for ablating tissue as claimed in claim 3, wherein said mirror includes a dielectric coating disposed on a reflective surface thereof.

5. An apparatus for ablating tissue as claimed in claim 1, wherein said causing means includes means for shifting said focused energy.

6. An apparatus for ablating tissue as claimed in claim 5, wherein said causing means includes a galvanometer connected to said directing means.

7. An apparatus for ablating tissue as claimed in claim 2, wherein:

said directing means includes means for directing said pulsed laser beam on half of the optical fibers in said array; and said causing means includes means for causing said laser beam to irradiate sequential halves of said proximal end of said array.

8. An apparatus for ablating tissue as claimed in claim 1, wherein said array of optical fibers includes an optical fiber matrix at least two fibers wide and n fibers long, with n being greater than two.

9. An apparatus for ablating tissue as claimed in claim 8, wherein alternate pulses from said producing means irradiate part of said matrix dimensioned one by n; and wherein remaining pulses from said producing means irradiate a different part of said matrix dimensioned one by n.

10. An apparatus for ablating tissue as claimed in claim 1, wherein said linear array of optical fibers includes a plurality of optical fiber bundles disposed along a common transverse axis.

11. An apparatus for ablating tissue as claimed in claim 10, wherein said plurality of optical fiber bundles includes two bundles of optical fibers.

12. An apparatus for ablating tissue as claimed in claim 10, wherein said plurality of optical fiber bundles includes three bundles of optical fibers.

13. An apparatus for ablating tissue as claimed in claim 1, wherein said linear array comprises a matrix of optical fibers one fiber wide and n fibers long, wherein n is greater than three.

14. An apparatus for ablating tissue as claimed in claim 1, wherein said causing means includes means for shifting said optical fibers.

15. An apparatus for ablating tissue comprising:

a pulsed energy source;

means for focusing said energy;

a bundle of optical fibers, a proximal end of said fibers being disposed in an array;

means for directing said focused energy on a group of at least two and less than all of said fibers; and linear scanning means for causing said directing means to sequentially direct said focused energy in synchronism with individual pulses of said energy on different groups of said optical fibers;

wherein said causing means includes means for shifting said optical fibers; and wherein said causing means includes a piezo electric stack.

16. An apparatus for ablating tissue as claimed in claim 1, wherein said causing means includes means for shifting energy along a longitudinal axis of said proximal end of said bundle of optical fibers.

17. An apparatus for ablating tissue as claimed in claim 1, including means for shifting energy in a direction perpendicular to a longitudinal axis of said proximal end of said bundle of optical fibers.

18. An apparatus for ablating tissue, comprising:

a catheter assembly including a plurality of optical fibers having proximal ends disposed in an array;

a pulsed excimer laser for outputting laser pulses;

means for focusing each laser pulse; and linear scanning means for directing successive pulses at different portions of said array, wherein each of said pulses irradiates at least two and less than all of said optical fibers, each optical fiber being irradiated by said pulse receiving sufficient radiation to ablate tissue at its distal end;

wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

19. An apparatus for ablating tissue as claimed in claim 18, wherein said directing means includes means for shifting said successive pulses.

20. An apparatus for ablating tissue as claimed in claim 19, wherein said shifting means includes a galvanometer.

21. An apparatus for ablating tissue as claimed in claim 20, wherein said directing means further includes a mirror that is moved by said galvanometer.

22. An apparatus for ablating tissue as claimed in claim 21, wherein said mirror includes a reflective dielectric coating.

23. An apparatus for ablating tissue as claimed in claim 18, wherein said directing means includes means for shifting said array.

24. An apparatus for ablating tissue, comprising:

a catheter assembly including a plurality of optical fibers having proximal ends disposed in an array;

a pulsed excimer laser for outputting laser pulses;

means for focusing each laser pulse; and linear scanning means for directing successive pulses at different portions of said array, said scanning means moving in synchronism with said laser's output pulses, wherein each of said pulses irradiates at least two and less than all of said optical fibers, each optical fiber being irradiated by said pulse receiving sufficient radiation to ablate tissue at its distal end;

wherein said directing means includes a piezo electric stack.

25. An apparatus for ablating tissue as claimed in claim 18, wherein said directing means includes means for shifting energy along a longitudinal axis of said proximal end of said plurality of optical fibers.

26. An apparatus for ablating tissue as claimed in claim 18, wherein said directing means includes means for shifting energy in a direction perpendicular to a longitudinal axis of said proximal end of said bundle of optical fibers.

27. An apparatus for ablating tissue as claimed in claim 18, wherein substantially all of said optical fibers that are irradiated simultaneously are disposed adjacently at a distal end of said catheter assembly.

28. An apparatus for ablating tissue, comprising:
a catheter assembly including a plurality of optical fibers having proximal ends disposed in an array;
a pulsed excimer laser for outputting laser pulses;
means for focusing each laser pulse; and
linear scanning means for directing successive pulses at different portions of said array, said scanning means moving in synchronism with said laser's output pulses, wherein each of said pulses irradiates at least two and less than all of said optical fibers, each optical fiber being irradiated by said pulse receiving sufficient radiation to ablate tissue at its distal end;
wherein said catheter assembly includes a coupler for coupling said laser pulses to said optical fibers, said catheter assembly comprising a female receptacle and a male plug portion.

29. An apparatus for ablating tissue as claimed in claim 18, wherein said plurality of optical fibers have a distal end disposed in a substantially circular bundle; and
wherein for each portion of the array that is a irradiated by said laser, the distal end of said catheter includes a group of adjacent fibers that output said laser pulse.

30. An apparatus for ablating tissue as claimed in claim 18, wherein said array of optical fibers includes an optical fiber matrix at least two fibers wide and n fibers long, with n being greater than two.

31. An apparatus for ablating tissue as claimed in claim 30, wherein alternate pulses from said producing means irradiate part of said matrix dimensioned one by n; and
wherein remaining pulses from said producing means irradiate a different part of said matrix dimensioned one by n.

32. An apparatus for ablating tissue as claimed in claim 18, wherein said linear array of optical fibers includes a plurality of optical fiber bundles disposed along a common transverse axis.

33. An apparatus for ablating tissue as claimed in claim 32, wherein said plurality of optical fiber bundles includes two bundles of optical fibers.

34. An apparatus for ablating tissue as claimed in claim 32, wherein said plurality of optical fiber bundles includes three bundles of optical fibers.

35. An apparatus for ablating tissue as claimed in claim 18, wherein said array comprises a matrix of optical fibers one fiber wide and n fibers long, wherein n is greater than three.

36. An apparatus for ablating tissue and for reducing the energy applied to tissue while maintaining a fluence level sufficient for ablation, comprising:
means for producing a laser beam;
means for focusing said laser beam;
a bundle of optical fibers, a proximal end of said fibers being disposed in an array;
means for directing said focused laser beam on a group of at least two and less than all of said fibers; and
means for causing said directing means to sequentially direct said focused laser beam on different groups of said optical fibers;
wherein said optical fibers receive less energy than is necessary to produce a fluence in all the fibers simultaneously to ablate tissue; and
wherein said directing means directs said laser beam so that each fiber of the group irradiated outputs radiation having a sufficiently high fluence to ablate tissue.

37. An apparatus for ablating tissue as claimed in claim 36, wherein:
said producing means includes means for producing a pulsed laser beam; and
said causing means causes said directing means to sequentially direct said focused laser beam on different groups of optical fibers after each pulse.

38. An apparatus for ablating tissue as claimed in claim 37, wherein said producing means is an excimer laser.

39. An apparatus for ablating tissue as claimed in claim 36, wherein said causing means includes means for shifting said fibers.

40. An apparatus for ablating tissue as claimed in claim 39, wherein said causing means includes a piezo electric stack.

41. An apparatus for ablating tissue as claimed in claim 36, wherein said causing means includes means for shifting said beam along a longitudinal axis of said proximal end of said bundle of optical fibers.

42. An apparatus for ablating tissue as claimed in claim 36, wherein said causing means includes means for shifting said beam in a direction perpendicular to a longitudinal axis of said proximal end of said bundle of optical fibers.

43. An apparatus for ablating tissue as claimed in claim 36, wherein substantially all of said optical fibers that are irradiated simultaneously are disposed adjacently at a distal end of said bundle of optical fibers.

44. An apparatus for ablating tissue as claimed in claim 36, wherein said directing means is a mirror.

45. An apparatus for ablating tissue as claimed in claim 44, wherein said mirror includes a dielectric coating disposed on a reflective surface thereof.

46. An apparatus for ablating tissue as claimed in claim 36, wherein said causing means includes a galvanometer.

47. An apparatus for ablating tissue as claimed in claim 37, wherein:
said directing means directs said pulsed laser beam on half of the optical fibers in said array; and
said causing means includes means for causing said laser beam to irradiate sequential halves of said proximal end of said array.

48. An apparatus for ablating tissue as claimed in claim 47, wherein said array of optical fibers includes an optical fiber matrix at least two fibers wide and n fibers long, with n being greater than two.

49. An apparatus for ablating tissue as claimed in claim 48, wherein alternate pulses from said producing means irradiate part of said matrix dimensioned one by n; and wherein remaining pulses from said producing means irradiate a different part of said matrix dimensioned one by n.

50. An apparatus for ablating tissue as claimed in claim 47, wherein said array of optical fibers includes a plurality of optical fiber bundles disposed along a common transverse axis.

51. An apparatus for ablating tissue as claimed in claim 50, wherein said plurality of optical fiber bundles includes two bundles of optical fibers.

52. An apparatus for ablating tissue as claimed in claim 50, wherein said plurality of optical fiber bundles includes three bundles of optical fibers.

53. An apparatus for ablating tissue as claimed in claim 47, wherein said linear array comprises a matrix of optical fibers one fiber wide and n fibers long, wherein n is greater than three.

54. A method of ablating tissue, comprising the steps of:
focusing radiant energy;
directing said focused energy onto one section of a bundle of optical fibers having a proximal end with the fibers disposed in an array; and
sequentially causing said focused energy to irradiate different sections of said proximal end, each of said sections containing at least two and less than all of said fibers;
wherein said optical fibers receive less energy than is necessary to produce a fluence in all the fibers simultaneously to ablate tissue; and
wherein said directing means directs said laser beam so that each fiber of the group irradiated outputs radiation having a sufficiently high fluence to ablate tissue.

55. A method of ablating tissue as claimed in claim 54, wherein said producing step includes producing a pulsed laser beam.

56. A method of ablating tissue as claimed in claim 54, wherein said causing step includes the step of shifting said energy.

57. A method of ablating tissue as claimed in claim 54, wherein said causing step includes the step of shifting said optical fibers.

58. A method of ablating tissue, comprising the steps of:
focusing radiant energy;
directing said focused energy onto one section of a bundle of optical fibers having a proximal end with the fibers disposed in an array; and
sequentially causing said focused energy to irradiate different sections of said proximal end, each of said sections containing at least two and less than all of said fibers;
wherein said focused energy irradiates said sections in synchronism with bursts of radiant energy;
wherein said causing step includes the step of shifting said optical fibers;
wherein said shifting step includes using a piezo electric stack.

59. A method of ablating tissue as claimed in claim 54, wherein said causing step includes the step of shifting energy along a longitudinal axis of said proximal end of said bundle of fibers.

60. A method of ablating tissue as claimed in claim 54, wherein said causing step includes the step of shifting energy in a direction perpendicular to a longitudinal axis of said proximal end of said bundle of fibers.

61. A method of ablating tissue as claimed in claim 54, wherein said directing step includes positioning a mirror to direct said laser beam.

62. A method of ablating tissue as claimed in claim 61, wherein said sequentially causing step includes the step of first irradiating said one section, said one section being half of a total number of fibers in said array and then irradiating another section, said another section being half the total number of optical fibers in said array, said one and another sections being separate halves of said array.

63. A method of ablating tissue according to claim 54, wherein said directing step includes providing said bundle of optical fibers having a proximal end disposed in said array that includes an optical fiber matrix at least two fibers wide and n fibers long, with n being greater than two.

64. A method of ablating tissue according to claim 63, wherein said causing step includes irradiating part of said matrix dimensioned one by n with alternate pulses of said laser beam; and
irradiating a different part of said matrix dimensioned one by n with remaining pulses of said laser beam.

65. A method of ablating tissue according to claim 54, wherein said directing step includes providing said bundle of optical fibers having a proximal end disposed in said array that includes a plurality of optical fiber bundles disposed along a common transverse axis.

66. A method of ablating tissue according to claim 65, wherein said providing step includes providing three bundles of optical fibers.

67. A method of ablating tissue according to claim 65, wherein said providing step includes providing two bundles of optical fibers.

68. A method of inserting a bundle of fibers into a groove on a substrate, said method comprising the steps of:
trimming tail tubing covering the bundle so as to expose a first length of optical fibers;
forming a glue plug proximate an end of the tail tubing, said glue plug being formed on said first length;
applying a potting material to a second length at an end of said bundle so as to support said exposed fibers;
forming a piece of shrink tubing over the second length to provide extra support;
cutting through the potted area using a diamond saw and polishing the cut end of said bundle;
removing the shrink tubing and potting material from said bundle;
heating the bundle and stripping a third length of polyimide coating from the exposed fibers;
forming a second piece of shrink tubing on said bundle, said second piece extending from said tail tubing onto said third length;
wetting the fibers with purified water and then inserting the bundle into the groove on the substrate, with fibers making up the third length extending so that the tip of the third length is flush with an edge of the substrate;
tacking the bundle to the substrate;
applying pressure to said third length, forming said fibers making up said third length into a rectangular close pack and tacking the third length into the groove proximate an edge of the groove; and
potting the bundle with fiber guard and handle.

69. An apparatus for ablating tissue comprising:

an excimer laser for producing a pulsed output beam;
means for focusing the output beam;
a bundle of optical fibers;
a female coupling portion for receiving the focused output beam;
a male coupling portion, a proximal end of said optical fibers being attached to said male coupling portion in a linear array, said male coupling portion being detachably coupled to said female coupling portion; and
means for scanning said focused output beam across said optical fibers in synchronism with successive pulses of said excimer laser so as to allow said successive pulses to irradiate at least two and less than all of said fibers and so that successive pulses irradiate different fibers;
wherein said male coupling portion includes a substrate having fibers disposed thereon and a cover slide covering said fibers, said substrate and cover slide being attached to a handle portion of said male coupling portion;
wherein said female coupling portion includes a spring plunger and first and second reference balls for positioning said male coupling portion within said female coupling portion.

70. An apparatus for ablating tissue as claimed in claim 19, wherein said shifting means includes a stepper motor.

71. A method of laying a linear array of optical fibers, comprising the steps of:
sorting the optical fibers into as many bundles as there are groups of fibers to be irradiated, the number of groups being at least two;
placing a piece of shrink wrap tubing over the optical fibers;
placing the optical fibers onto a substrate such that adjacent fiber bundles are separated from one another by a gap, and wherein the optical fibers overhang the end of the substrate by a first length;
fixing the tubing to the substrate using an adhesive;
spreading the fibers into a single row while simultaneously maintaining the space between the groups;
fixing the fibers to the substrate using an adhesive;
cutting the first length optical fibers; and
polishing the optical fibers.

72. An apparatus for ablating tissue, comprising:
means for producing energy;
means for focusing said energy;
a bundle of optical fibers having a proximal end disposed in an array;
means for coupling said focused energy into said array, said coupling means including a male plug portion and a female receptacle for receiving the male plug portion; and
means for scanning said focused energy over said array, said scanning means irradiating at least two and less than all of said optical fibers and sequentially directing said focused energy on different groups of said optical fibers;
wherein said scanning means operates so as to be synchronous with bursts of said energy.

73. An apparatus for ablating tissue as claimed in claim 72, wherein the male plug portion includes:
means for grasping said male plug portion;
means for indicating a size of said optical fiber bundle disposed on said grasping means;
means for joining said male plug portion to said female receptacle extending from said grasping means; and
means for maintaining said optical fibers in said array.

74. An apparatus for ablating tissue as claimed in claim 73, wherein said grasping means includes an enlarged handle portion.

75. An apparatus for ablating tissue as claimed in claim 73, wherein said indicating means includes pins that protrude from said grasping means towards said female receptacle.

76. An apparatus for ablating tissue as claimed in claim 73, wherein said joining means includes a first plate having said fibers disposed thereon and a second plate disposed on said first plate for protecting said optical fibers, said first and second plates extending from said grasping means.

77. An apparatus for ablating tissue as claimed in claim 76, wherein said maintaining means includes a plurality of grooves disposed on said first plate.

78. An apparatus for ablating tissue as claimed in claim 77, wherein said array is disposed in a plurality of grooves on said first plate.

79. An apparatus for ablating tissue as claimed in claim 77, wherein said array is disposed in two grooves on said first plate.

80. An apparatus for ablating tissue as claimed in claim 72, wherein said female receptacle includes:
means for generating a unique signal indicative of the size of said bundle of optical fibers;
means for repeatably positioning said male plug portion in a position so that said scanning means may irradiate said array; and
means for blocking said energy so that said energy does not pass through said female receptacle when said male plug portion is not joined thereto.

81. An apparatus for ablating tissue as claimed in claim 80, wherein said generating means includes a microswitch housed within said female receptacle, said microswitch producing said unique signal via interaction with said male plug portion.

82. An apparatus for ablating tissue as claimed in claim 80, wherein said positioning means includes at least one reference ball and a spring plunger.

83. An apparatus for ablating tissue as claimed in claim 82, wherein said positioning means includes a first reference ball disposed opposite said spring plunger and a second reference ball disposed in said female receptacle.

84. An apparatus for ablating tissue as claimed in claim 82, wherein said male plug portion is adapted so as to accommodate said spring plunger in a recess formed on a surface thereof.

85. An apparatus for ablating tissue as claimed in claim 80, wherein said blocking means includes a spring biased steel shutter attached to a rear portion of the female receptacle, said steel shutter being flattened by insertion of said male plug portion into said female receptacle.

86. An apparatus for ablating tissue comprising:
means for producing a laser beam;
means for focusing said laser beam;
an array of optical fibers;
means for coupling said focused laser beam to said array of optical fibers, said coupling means including a male portion to which said array is attached via grooves in said male portion, each of said grooves containing at least two optical fibers of said array and a female portion receiving said focused laser beam; and means for directing said laser beam onto at least two but less than all of said plurality of optical fibers, said directing means generating relative movement between said array of optical fibers and said focused laser beam so that said focused laser beam is directed onto different optical fibers of said array.

87. An apparatus for ablating tissue as claimed in claim 86, wherein said directing means includes a piezo electric stack that moves said array in response to signals from a computer.

88. An apparatus for ablating tissue as claimed in claim 86, wherein said directing means includes a mirror for reflecting said focused beam and a stepper motor for moving said mirror.

89. An apparatus for ablating tissue as claimed in claim 86, wherein said directing means includes a galvanometer.

90. An apparatus for ablating tissue as claimed in claim 86, wherein said male portion comprises:
means for grasping said male portion; and
means for interacting with said female portion so as to provide a signal indicative of a size of said fiberoptic catheter.

91. An apparatus for ablating tissue as claimed in claim 90, wherein said interacting means includes pins disposed on said grasping means, said pins being inserted in said female portion.

92. An apparatus for ablating tissue as claimed in claim 86, wherein said female portion includes:
means for positioning said male portion in said female portion;
means for generating a signal indicative of the size of said catheter, said generating means being responsive to external interactions; and
means for blocking said laser beam when said male portion is not disposed in said female portion.

93. A male coupling portion for a fiberoptic catheter, comprising a first plate member having a plurality of grooves disposed thereon, said grooves for retaining a plurality of optical fibers, wherein said plurality of optical fiber is divided such that each groove contains at least two optical fibers.

94. A male coupling portion for a fiberoptic catheter as claimed in claim 93, further comprising a second plate disposed parallel to said first plate.

95. A male coupling portion for a fiberoptic catheter as claimed in claim 94, further comprising a notch formed in said second plate.

96. A male coupling portion for a fiberoptic catheter as claimed in claim 93, further comprising means for indicating a size of a catheter attached to said male coupling portion.

97. A coupling apparatus for coupling a laser to a laser catheter, said coupling apparatus including a male portion and a female portion;
wherein said male portion comprises:
a handle portion having an optical fiber catheter extending therefrom;
a first plate member attached to said handle having optical fibers of said catheter disposed in an array on a first surface thereof, said fibers being disposed in grooves formed on said first surface;
a second plate member attached to said handle so as to oppose said first plate; and
size indicating means for indicating a size of said optical fiber catheter; and wherein said female portion comprises:
means for interacting with said size indicating means and for providing a signal indicative of the size of the catheter;
means for repeatably positioning said male portion in a position so that laser energy may be coupled to said catheter; and
means for blocking said energy when said male and female portions are not coupled.

98. A coupling apparatus as claimed in claim 97, wherein said size indicating means includes at least one pin protruding from said handle in a direction so as to enter receiving holes disposed in said female portion.

99. A coupling apparatus as claimed in claim 98, wherein said means for interacting and providing includes a microswitch disposed in said female portion, said microswitch contacting said at least one pin.

100. A coupling apparatus as claimed in claim 97, wherein said means for interacting and providing includes a microswitch disposed in said female portion.

101. A coupling apparatus as claimed in claim 97, wherein said means for blocking includes a steel spring shutter.

102. A coupling apparatus as claimed in claim 97, wherein said means for repeatably positioning includes a first and a second reference ball for guiding the male portion into the female portion and a spring plunger for pressing the male portion into a predetermined position.

103. A coupling apparatus as claimed in claim 102, wherein said spring plunger enters into a groove on said second plate member to hold said male portion in position.

104. A coupling apparatus as claimed in claim 97, wherein said first plate member has two grooves formed on said first surface.

105. A coupling apparatus as claimed in claim 97, wherein said first plate member has three grooves formed on said first surface.

106. An excimer laser joined to a fiberoptic catheter via a coupling apparatus as claimed in claim 97.

107. An apparatus for ablating tissue comprising:
means for producing energy and for focusing said energy;
an array of optical fibers;
means for coupling said focused energy to said array of optical fibers, said coupling means including a male portion to which said array is attached and a female portion receiving said focused laser beam;
means for directing said laser beam onto at least two but less than all of said plurality of optical fibers;
wherein said directing means is a piezo electric stack and generates relative movement between said array of optical fibers and said focused laser beam so that said focused laser beam is directed onto different optical fibers of said array in synchronism with pulses from said laser.

108. An apparatus for ablating tissue, comprising:
a pulsed energy source;
means for focusing said energy;
a bundle of optical fibers, a proximal end of said fibers being disposed in an array;
means for directing said focused energy on a group of at least two and less than all of said fibers; and
linear scanning means for causing said directing means to sequentially direct said focused energy on different groups of said optical fibers;

wherein said bundle of optical fibers includes a plurality of optical fiber sub-bundles disposed in separate grooves on a fiber holding device.

109. An apparatus for ablating tissue as claimed in claim 15, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

110. An apparatus for ablating tissue as claimed in claim 24, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

111. An apparatus for ablating tissue as claimed in claim 28, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

112. A method for ablating tissue as claimed in claim 58, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

113. An apparatus for ablating tissue as claimed in claim 69, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

114. An apparatus for ablating tissue as claimed in claim 72, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

115. An apparatus for ablating tissue as claimed in claim 86, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

116. An apparatus for ablating tissue as claimed in claim 107, wherein said optical fibers receive less energy than is necessary to produce a fluence in all the fibers simultaneously to ablate tissue; and wherein said directing means directs said laser beam so that each fiber of the group irradiated outputs radiation having a sufficiently high fluence to ablate tissue.

* * * * *